(12) United States Patent
Fox

(10) Patent No.: US 8,252,057 B2
(45) Date of Patent: Aug. 28, 2012

(54) SURGICAL ACCESS DEVICE

(75) Inventor: William D. Fox, New Richmond, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 821 days.

(21) Appl. No.: 12/362,826

(22) Filed: Jan. 30, 2009

(65) Prior Publication Data
US 2010/0198005 A1 Aug. 5, 2010

(51) Int. Cl.
*A61F 2/44* (2006.01)
(52) U.S. Cl. .................................. 623/17.12
(58) Field of Classification Search .......... 606/191–198; 623/1.11; 604/96.01, 101.01–101.03; 600/102–104, 600/108, 113, 116, 121, 124, 125
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,383,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |

(Continued)

FOREIGN PATENT DOCUMENTS
AU 666310 B2 2/1996
(Continued)

OTHER PUBLICATIONS

International Preliminary Report on Patentability for PCT/US2010/022181, Aug. 2, 2011 (10 pages).

(Continued)

*Primary Examiner* — Kevin T Truong

(57) ABSTRACT

A surgical access device comprises a conduit comprising a proximal portion and a distal portion. An inflatable member at least partially surrounds a portion of the conduit and is positioned proximate to the distal portion of the conduit. In various embodiments, a protective sleeve can at least partially surround a portion of the conduit and is movable between at least a first position and a second position. In at least one embodiment, the protective sleeve is configured to at least partially cover the inflatable member when in the first position and is configured to expose the inflatable member when in the second position.

19 Claims, 12 Drawing Sheets

U.S. PATENT DOCUMENTS

| | | |
|---|---|---|
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |

| | | |
|---|---|---|
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,911,737 A | 6/1999 | Lee et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |

| | | | | | | |
|---|---|---|---|---|---|---|
| 5,944,718 | A | 8/1999 | Austin et al. | 6,277,136 B1 | 8/2001 | Bonutti |
| 5,951,549 | A | 9/1999 | Richardson et al. | 6,283,963 B1 | 9/2001 | Regula |
| 5,954,720 | A | 9/1999 | Wilson et al. | 6,293,909 B1 | 9/2001 | Chu et al. |
| 5,954,731 | A | 9/1999 | Yoon | 6,293,952 B1 | 9/2001 | Brosens et al. |
| 5,957,943 | A | 9/1999 | Vaitekunas | 6,296,630 B1 | 10/2001 | Altman et al. |
| 5,957,953 | A | 9/1999 | DiPoto et al. | 6,322,578 B1 | 11/2001 | Houle et al. |
| 5,971,995 | A | 10/1999 | Rousseau | 6,326,177 B1 | 12/2001 | Schoenbach et al. |
| 5,976,074 | A | 11/1999 | Moriyama | 6,328,730 B1 | 12/2001 | Harkrider, Jr. |
| 5,976,075 | A | 11/1999 | Beane et al. | 6,350,267 B1 | 2/2002 | Stefanchik |
| 5,976,130 | A | 11/1999 | McBrayer et al. | 6,350,278 B1 | 2/2002 | Lenker et al. |
| 5,976,131 | A | 11/1999 | Guglielmi et al. | 6,352,503 B1 | 3/2002 | Matsui et al. |
| 5,980,539 | A | 11/1999 | Kontos | 6,352,543 B1 | 3/2002 | Cole |
| 5,980,556 | A | 11/1999 | Giordano et al. | 6,355,035 B1 | 3/2002 | Manushakian |
| 5,984,938 | A | 11/1999 | Yoon | 6,361,534 B1 | 3/2002 | Chen et al. |
| 5,984,939 | A | 11/1999 | Yoon | 6,371,956 B1 | 4/2002 | Wilson et al. |
| 5,989,182 | A | 11/1999 | Hori et al. | 6,379,366 B1 | 4/2002 | Fleischman et al. |
| 5,993,447 | A | 11/1999 | Blewett et al. | 6,383,195 B1 | 5/2002 | Richard |
| 5,997,555 | A | 12/1999 | Kontos | 6,383,197 B1 | 5/2002 | Conlon et al. |
| 6,001,120 | A | 12/1999 | Levin | 6,391,029 B1 | 5/2002 | Hooven et al. |
| 6,004,269 | A | 12/1999 | Crowley et al. | 6,402,735 B1 | 6/2002 | Langevin |
| 6,004,330 | A | 12/1999 | Middleman et al. | 6,406,440 B1 | 6/2002 | Stefanchik |
| 6,007,566 | A | 12/1999 | Wenstrom, Jr. | 6,409,733 B1 | 6/2002 | Conlon et al. |
| 6,010,515 | A | 1/2000 | Swain et al. | 6,427,089 B1 | 7/2002 | Knowlton |
| 6,012,494 | A | 1/2000 | Balazs | 6,431,500 B1 | 8/2002 | Jacobs et al. |
| 6,017,356 | A | 1/2000 | Frederick et al. | 6,443,970 B1 | 9/2002 | Schulze et al. |
| 6,019,770 | A | 2/2000 | Christoudias | 6,443,988 B2 * | 9/2002 | Felt et al. .................. 623/17.12 |
| 6,024,708 | A | 2/2000 | Bales et al. | 6,447,511 B1 | 9/2002 | Slater |
| 6,024,747 | A | 2/2000 | Kontos | 6,447,523 B1 | 9/2002 | Middleman et al. |
| 6,027,522 | A | 2/2000 | Palmer | 6,454,783 B1 | 9/2002 | Piskun |
| 6,030,365 | A | 2/2000 | Laufer | 6,454,785 B2 | 9/2002 | De Hoyos Garza |
| 6,030,634 | A | 2/2000 | Wu et al. | 6,458,076 B1 | 10/2002 | Pruitt |
| 6,033,399 | A | 3/2000 | Gines | 6,464,701 B1 | 10/2002 | Hooven et al. |
| 6,036,685 | A | 3/2000 | Mueller | 6,464,702 B2 | 10/2002 | Schulze et al. |
| 6,053,927 | A | 4/2000 | Hamas | 6,475,104 B1 | 11/2002 | Lutz et al. |
| 6,066,160 | A | 5/2000 | Colvin et al. | 6,485,411 B1 | 11/2002 | Konstorum et al. |
| 6,068,603 | A | 5/2000 | Suzuki | 6,489,745 B1 | 12/2002 | Koreis |
| 6,068,629 | A | 5/2000 | Haissaguerre et al. | 6,491,626 B1 | 12/2002 | Stone et al. |
| 6,071,233 | A | 6/2000 | Ishikawa et al. | 6,491,627 B1 | 12/2002 | Komi |
| 6,074,408 | A | 6/2000 | Freeman | 6,491,691 B1 | 12/2002 | Morley et al. |
| 6,086,530 | A | 7/2000 | Mack | 6,493,590 B1 | 12/2002 | Wessman et al. |
| 6,090,108 | A | 7/2000 | McBrayer et al. | 6,494,893 B2 | 12/2002 | Dubrul et al. |
| 6,096,046 | A | 8/2000 | Weiss | 6,500,176 B1 | 12/2002 | Truckai et al. |
| 6,102,926 | A | 8/2000 | Tartaglia et al. | 6,503,192 B1 | 1/2003 | Ouchi |
| 6,106,473 | A | 8/2000 | Violante et al. | 6,506,190 B1 | 1/2003 | Walshe |
| 6,109,852 | A | 8/2000 | Shahinpoor et al. | 6,508,827 B1 | 1/2003 | Manhes |
| 6,110,154 | A | 8/2000 | Shimomura et al. | 6,520,954 B2 | 2/2003 | Ouchi |
| 6,110,183 | A | 8/2000 | Cope | 6,543,456 B1 | 4/2003 | Freeman |
| 6,113,593 | A | 9/2000 | Tu et al. | 6,551,270 B1 | 4/2003 | Bimbo et al. |
| 6,117,144 | A | 9/2000 | Nobles et al. | 6,554,829 B2 | 4/2003 | Schulze et al. |
| 6,117,158 | A | 9/2000 | Measamer et al. | 6,558,384 B2 | 5/2003 | Mayenberger |
| 6,139,555 | A | 10/2000 | Hart et al. | 6,562,035 B1 | 5/2003 | Levin |
| 6,146,391 | A | 11/2000 | Cigaina | 6,562,052 B2 | 5/2003 | Nobles et al. |
| 6,148,222 | A | 11/2000 | Ramsey, III | 6,569,159 B1 | 5/2003 | Edwards et al. |
| 6,149,653 | A | 11/2000 | Deslauriers | 6,572,629 B2 | 6/2003 | Kalloo et al. |
| 6,149,662 | A | 11/2000 | Pugliesi et al. | 6,572,635 B1 | 6/2003 | Bonutti |
| 6,159,200 | A | 12/2000 | Verdura et al. | 6,575,988 B2 | 6/2003 | Rousseau |
| 6,165,184 | A | 12/2000 | Verdura et al. | 6,579,311 B1 | 6/2003 | Makower |
| 6,168,570 | B1 | 1/2001 | Ferrera | 6,585,642 B2 | 7/2003 | Christopher |
| 6,168,605 | B1 | 1/2001 | Measamer et al. | 6,585,717 B1 | 7/2003 | Wittenberger et al. |
| 6,170,130 | B1 | 1/2001 | Hamilton et al. | 6,592,559 B1 | 7/2003 | Pakter et al. |
| 6,179,776 | B1 | 1/2001 | Adams et al. | 6,592,603 B2 | 7/2003 | Lasner |
| 6,179,837 | B1 | 1/2001 | Hooven | 6,602,262 B2 | 8/2003 | Griego et al. |
| 6,183,420 | B1 | 2/2001 | Douk et al. | 6,605,105 B1 | 8/2003 | Cuschieri et al. |
| 6,190,353 | B1 | 2/2001 | Makower et al. | 6,610,072 B1 | 8/2003 | Christy et al. |
| 6,190,384 | B1 | 2/2001 | Ouchi | 6,610,074 B2 | 8/2003 | Santilli |
| 6,190,399 | B1 | 2/2001 | Palmer et al. | 6,620,193 B1 | 9/2003 | Lau et al. |
| 6,203,533 | B1 | 3/2001 | Ouchi | 6,623,448 B2 | 9/2003 | Slater |
| 6,206,872 | B1 | 3/2001 | Lafond et al. | 6,626,919 B1 | 9/2003 | Swanstrom |
| 6,206,877 | B1 | 3/2001 | Kese et al. | 6,632,229 B1 | 10/2003 | Yamanouchi |
| 6,214,007 | B1 | 4/2001 | Anderson | 6,638,266 B2 | 10/2003 | Wilson et al. |
| 6,228,096 | B1 | 5/2001 | Marchand | 6,652,521 B2 | 11/2003 | Schulze |
| 6,234,958 | B1 | 5/2001 | Snoke et al. | 6,652,551 B1 | 11/2003 | Heiss |
| 6,245,079 | B1 | 6/2001 | Nobles et al. | 6,656,194 B1 | 12/2003 | Gannoe et al. |
| 6,246,914 | B1 | 6/2001 | de la Rama et al. | 6,663,641 B1 | 12/2003 | Kovac et al. |
| 6,258,064 | B1 | 7/2001 | Smith et al. | 6,666,854 B1 | 12/2003 | Lange |
| 6,261,242 | B1 | 7/2001 | Roberts et al. | 6,672,338 B1 | 1/2004 | Esashi et al. |
| 6,264,664 | B1 | 7/2001 | Avellanet | 6,673,058 B2 | 1/2004 | Snow |
| 6,270,497 | B1 | 8/2001 | Sekino et al. | 6,673,087 B1 | 1/2004 | Chang et al. |
| 6,270,505 | B1 | 8/2001 | Yoshida et al. | 6,679,882 B1 | 1/2004 | Kornerup |

| | | |
|---|---|---|
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 * | 4/2005 | Di Caprio et al. ............ 606/192 |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |

| | | |
|---|---|---|
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,674,259 B2 | 3/2010 | Shadduck |
| 7,713,189 B2 | 5/2010 | Hanke |
| 7,713,270 B2 | 5/2010 | Suzuki |
| 7,721,742 B2 * | 5/2010 | Kalloo et al. ............ 604/101.01 |
| 7,736,374 B2 | 6/2010 | Vaughan et al. |
| 7,744,615 B2 | 6/2010 | Couture |
| 7,758,577 B2 | 7/2010 | Nobis et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,075,587 B2 | 12/2011 | Ginn |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |

| | | | | | |
|---|---|---|---|---|---|
| 2005/0033333 A1 | 2/2005 | Smith et al. | 2006/0058776 A1 | 3/2006 | Bilsbury |
| 2005/0043690 A1 | 2/2005 | Todd | 2006/0069396 A1 | 3/2006 | Meade et al. |
| 2005/0049616 A1 | 3/2005 | Rivera et al. | 2006/0069424 A1 | 3/2006 | Acosta et al. |
| 2005/0065397 A1 | 3/2005 | Saadat et al. | 2006/0069425 A1 | 3/2006 | Hillis et al. |
| 2005/0065517 A1 | 3/2005 | Chin | 2006/0074413 A1 | 4/2006 | Behzadian |
| 2005/0070754 A1 | 3/2005 | Nobis et al. | 2006/0079890 A1 | 4/2006 | Guerra |
| 2005/0070763 A1 | 3/2005 | Nobis et al. | 2006/0089528 A1 | 4/2006 | Tartaglia et al. |
| 2005/0070764 A1 | 3/2005 | Nobis et al. | 2006/0095031 A1 | 5/2006 | Ormsby |
| 2005/0080413 A1 | 4/2005 | Canady | 2006/0095060 A1 | 5/2006 | Mayenberger et al. |
| 2005/0085693 A1 | 4/2005 | Belson et al. | 2006/0100687 A1 | 5/2006 | Fahey et al. |
| 2005/0085832 A1 | 4/2005 | Sancoff et al. | 2006/0106423 A1 | 5/2006 | Weisel et al. |
| 2005/0090837 A1 | 4/2005 | Sixto, Jr. et al. | 2006/0111209 A1 | 5/2006 | Hinman et al. |
| 2005/0090838 A1 | 4/2005 | Sixto, Jr. et al. | 2006/0111210 A1 | 5/2006 | Hinman et al. |
| 2005/0101837 A1 | 5/2005 | Kalloo et al. | 2006/0111704 A1 | 5/2006 | Brenneman et al. |
| 2005/0101838 A1 | 5/2005 | Camillocci et al. | 2006/0129166 A1 | 6/2006 | Lavelle |
| 2005/0107663 A1 | 5/2005 | Saadat et al. | 2006/0135962 A1 | 6/2006 | Kick et al. |
| 2005/0107664 A1 | 5/2005 | Kalloo et al. | 2006/0135971 A1 | 6/2006 | Swanstrom et al. |
| 2005/0110881 A1 | 5/2005 | Glukhovsky et al. | 2006/0135984 A1 | 6/2006 | Kramer et al. |
| 2005/0113847 A1 | 5/2005 | Gadberry et al. | 2006/0142644 A1 | 6/2006 | Mulac et al. |
| 2005/0119613 A1 | 6/2005 | Moenning et al. | 2006/0142652 A1 | 6/2006 | Keenan |
| 2005/0124855 A1 | 6/2005 | Jaffe et al. | 2006/0142790 A1 | 6/2006 | Gertner |
| 2005/0125010 A1 | 6/2005 | Smith et al. | 2006/0142798 A1 | 6/2006 | Holman et al. |
| 2005/0131279 A1 | 6/2005 | Boulais et al. | 2006/0149131 A1 | 7/2006 | Or |
| 2005/0131457 A1 | 6/2005 | Douglas et al. | 2006/0149132 A1 | 7/2006 | Iddan |
| 2005/0137454 A1 | 6/2005 | Saadat et al. | 2006/0149135 A1 | 7/2006 | Paz |
| 2005/0143647 A1 | 6/2005 | Minai et al. | 2006/0161190 A1 | 7/2006 | Gadberry et al. |
| 2005/0143690 A1 | 6/2005 | High | 2006/0167416 A1 | 7/2006 | Mathis et al. |
| 2005/0143774 A1 | 6/2005 | Polo | 2006/0167482 A1 | 7/2006 | Swain et al. |
| 2005/0143803 A1 | 6/2005 | Watson et al. | 2006/0178560 A1 | 8/2006 | Saadat et al. |
| 2005/0149087 A1 | 7/2005 | Ahlberg et al. | 2006/0183975 A1 | 8/2006 | Saadat et al. |
| 2005/0149096 A1 | 7/2005 | Hilal et al. | 2006/0184161 A1 | 8/2006 | Maahs et al. |
| 2005/0159648 A1 | 7/2005 | Freed | 2006/0189844 A1 | 8/2006 | Tien |
| 2005/0165272 A1 | 7/2005 | Okada et al. | 2006/0189845 A1 | 8/2006 | Maahs et al. |
| 2005/0165378 A1 | 7/2005 | Heinrich et al. | 2006/0190027 A1 | 8/2006 | Downey |
| 2005/0165411 A1 | 7/2005 | Orban, III | 2006/0195084 A1 | 8/2006 | Slater |
| 2005/0165429 A1 | 7/2005 | Douglas et al. | 2006/0200005 A1 | 9/2006 | Bjork et al. |
| 2005/0182429 A1 | 8/2005 | Yamanouchi | 2006/0200169 A1 | 9/2006 | Sniffin |
| 2005/0192478 A1 | 9/2005 | Williams et al. | 2006/0200170 A1 | 9/2006 | Aranyi |
| 2005/0192598 A1 | 9/2005 | Johnson et al. | 2006/0200199 A1 | 9/2006 | Bonutti et al. |
| 2005/0192602 A1 | 9/2005 | Manzo | 2006/0217665 A1 | 9/2006 | Prosek |
| 2005/0192654 A1 | 9/2005 | Chanduszko et al. | 2006/0217697 A1 | 9/2006 | Lau et al. |
| 2005/0209624 A1 | 9/2005 | Vijay | 2006/0217742 A1 | 9/2006 | Messerly et al. |
| 2005/0215858 A1 | 9/2005 | Vail, III | 2006/0217743 A1 | 9/2006 | Messerly et al. |
| 2005/0216050 A1 | 9/2005 | Sepetka et al. | 2006/0229639 A1 | 10/2006 | Whitfield |
| 2005/0228406 A1 | 10/2005 | Bose | 2006/0229640 A1 | 10/2006 | Whitfield |
| 2005/0234297 A1 | 10/2005 | Devierre et al. | 2006/0237022 A1 | 10/2006 | Chen et al. |
| 2005/0250983 A1 | 11/2005 | Tremaglio et al. | 2006/0237023 A1 | 10/2006 | Cox et al. |
| 2005/0250990 A1 | 11/2005 | Le et al. | 2006/0241570 A1 | 10/2006 | Wilk |
| 2005/0250993 A1 | 11/2005 | Jaeger | 2006/0247576 A1 | 11/2006 | Poncet |
| 2005/0251166 A1 | 11/2005 | Vaughan et al. | 2006/0247673 A1 | 11/2006 | Voegele et al. |
| 2005/0251176 A1 | 11/2005 | Swanstrom et al. | 2006/0253004 A1 | 11/2006 | Frisch et al. |
| 2005/0261674 A1 | 11/2005 | Nobis et al. | 2006/0253039 A1 | 11/2006 | McKenna et al. |
| 2005/0267492 A1 | 12/2005 | Poncet et al. | 2006/0258907 A1 | 11/2006 | Stefanchik et al. |
| 2005/0272975 A1 | 12/2005 | McWeeney et al. | 2006/0258908 A1 | 11/2006 | Stefanchik et al. |
| 2005/0272977 A1 | 12/2005 | Saadat et al. | 2006/0258910 A1 | 11/2006 | Stefanchik et al. |
| 2005/0273084 A1 | 12/2005 | Hinman et al. | 2006/0258954 A1 | 11/2006 | Timberlake et al. |
| 2005/0277945 A1 | 12/2005 | Saadat et al. | 2006/0258955 A1 | 11/2006 | Hoffman et al. |
| 2005/0277951 A1 | 12/2005 | Smith et al. | 2006/0259010 A1 | 11/2006 | Stefanchik et al. |
| 2005/0277952 A1 | 12/2005 | Arp et al. | 2006/0264752 A1 | 11/2006 | Rubinsky et al. |
| 2005/0277954 A1 | 12/2005 | Smith et al. | 2006/0264904 A1 | 11/2006 | Kerby et al. |
| 2005/0277955 A1 | 12/2005 | Palmer et al. | 2006/0264930 A1 | 11/2006 | Nishimura |
| 2005/0277956 A1 | 12/2005 | Francese et al. | 2006/0270902 A1 | 11/2006 | Igarashi et al. |
| 2005/0277957 A1 | 12/2005 | Kuhns et al. | 2006/0271102 A1 | 11/2006 | Bosshard et al. |
| 2005/0283118 A1 | 12/2005 | Uth et al. | 2006/0276835 A1 | 12/2006 | Uchida |
| 2005/0283119 A1 | 12/2005 | Uth et al. | 2006/0281970 A1 | 12/2006 | Stokes et al. |
| 2005/0288555 A1 | 12/2005 | Binmoeller | 2006/0282106 A1 | 12/2006 | Cole et al. |
| 2006/0004406 A1 | 1/2006 | Wehrstein et al. | 2006/0285732 A1 | 12/2006 | Horn et al. |
| 2006/0004409 A1 | 1/2006 | Nobis et al. | 2006/0287644 A1 | 12/2006 | Inganas et al. |
| 2006/0004410 A1 | 1/2006 | Nobis et al. | 2006/0287666 A1 | 12/2006 | Saadat et al. |
| 2006/0015009 A1 | 1/2006 | Jaffe et al. | 2006/0293626 A1 | 12/2006 | Byrum et al. |
| 2006/0020167 A1 | 1/2006 | Sitzmann | 2007/0002135 A1 | 1/2007 | Glukhovsky |
| 2006/0020247 A1 | 1/2006 | Kagan et al. | 2007/0005019 A1 | 1/2007 | Okishige |
| 2006/0025654 A1 | 2/2006 | Suzuki et al. | 2007/0010801 A1 | 1/2007 | Chen et al. |
| 2006/0025781 A1 | 2/2006 | Young et al. | 2007/0015965 A1 | 1/2007 | Cox et al. |
| 2006/0025812 A1 | 2/2006 | Shelton, IV | 2007/0016225 A1 | 1/2007 | Nakao |
| 2006/0025819 A1 | 2/2006 | Nobis et al. | 2007/0032700 A1 | 2/2007 | Fowler et al. |
| 2006/0036267 A1 | 2/2006 | Saadat et al. | 2007/0032701 A1 | 2/2007 | Fowler et al. |
| 2006/0041188 A1 | 2/2006 | Dirusso et al. | 2007/0043261 A1 | 2/2007 | Watanabe et al. |
| 2006/0058582 A1 | 3/2006 | Maahs et al. | 2007/0043345 A1 | 2/2007 | Davalos et al. |

| | | |
|---|---|---|
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287206 A1 | 11/2009 | Jun |
| 2009/0287236 A1 | 11/2009 | Bakos et al. |

| | | | | | | |
|---|---|---|---|---|---|---|
| 2009/0292164 A1 | 11/2009 | Yamatani | | EP | 0286415 A2 | 10/1988 |
| 2009/0299135 A1 | 12/2009 | Spivey | | EP | 0589454 A2 | 3/1994 |
| 2009/0299143 A1 | 12/2009 | Conlon et al. | | EP | 0464479 B1 | 3/1995 |
| 2009/0299362 A1 | 12/2009 | Long et al. | | EP | 0529675 B1 | 2/1996 |
| 2009/0299385 A1 | 12/2009 | Stefanchik et al. | | EP | 0724863 B1 | 7/1999 |
| 2009/0299406 A1 | 12/2009 | Swain et al. | | EP | 0760629 B1 | 11/1999 |
| 2009/0299409 A1 | 12/2009 | Coe et al. | | EP | 0818974 B1 | 7/2001 |
| 2009/0306658 A1 | 12/2009 | Nobis et al. | | EP | 1281356 A2 | 2/2003 |
| 2009/0306683 A1 | 12/2009 | Zwolinski et al. | | EP | 0947166 B1 | 5/2003 |
| 2009/0322864 A1 | 12/2009 | Karasawa et al. | | EP | 0836832 B1 | 12/2003 |
| 2009/0326561 A1 | 12/2009 | Carroll, II et al. | | EP | 1402837 A1 | 3/2004 |
| 2010/0010294 A1 | 1/2010 | Conlon et al. | | EP | 0744918 B1 | 4/2004 |
| 2010/0010298 A1 | 1/2010 | Bakos et al. | | EP | 0931515 B1 | 8/2004 |
| 2010/0010299 A1 | 1/2010 | Bakos et al. | | EP | 0941128 B1 | 10/2004 |
| 2010/0010303 A1 | 1/2010 | Bakos | | EP | 1411843 B1 | 10/2004 |
| 2010/0010510 A1 | 1/2010 | Stefanchik | | EP | 1150614 B1 | 11/2004 |
| 2010/0010511 A1 | 1/2010 | Harris et al. | | EP | 1477104 A1 | 11/2004 |
| 2010/0023032 A1 | 1/2010 | Granja Filho | | EP | 1481642 A1 | 12/2004 |
| 2010/0036198 A1 | 2/2010 | Tacchino et al. | | EP | 1493391 A1 | 1/2005 |
| 2010/0042045 A1 | 2/2010 | Splvey | | EP | 0848598 B1 | 2/2005 |
| 2010/0048990 A1 | 2/2010 | Bakos | | EP | 1281360 B1 | 3/2005 |
| 2010/0049190 A1 | 2/2010 | Long et al. | | EP | 1568330 A1 | 8/2005 |
| 2010/0049223 A1 | 2/2010 | Granja Filho | | EP | 1452143 B1 | 9/2005 |
| 2010/0056861 A1 | 3/2010 | Spivey | | EP | 1616527 A2 | 1/2006 |
| 2010/0056862 A1 | 3/2010 | Bakos | | EP | 1006888 B1 | 3/2006 |
| 2010/0057085 A1 | 3/2010 | Holcomb et al. | | EP | 1629764 A1 | 3/2006 |
| 2010/0057108 A1 | 3/2010 | Spivey et al. | | EP | 1013229 B1 | 6/2006 |
| 2010/0063538 A1 | 3/2010 | Spivey et al. | | EP | 1721561 A1 | 11/2006 |
| 2010/0076451 A1 | 3/2010 | Zwolinski et al. | | EP | 1153578 B1 | 3/2007 |
| 2010/0081877 A1 | 4/2010 | Vakharia | | EP | 1334696 B1 | 3/2007 |
| 2010/0087813 A1 | 4/2010 | Long | | EP | 1769766 A1 | 4/2007 |
| 2010/0113872 A1 | 5/2010 | Asada et al. | | EP | 1836971 A2 | 9/2007 |
| 2010/0121362 A1 | 5/2010 | Clague et al. | | EP | 1836980 A1 | 9/2007 |
| 2010/0130817 A1 | 5/2010 | Conlon | | EP | 1854421 A2 | 11/2007 |
| 2010/0130975 A1 | 5/2010 | Long | | EP | 1857061 A1 | 11/2007 |
| 2010/0131005 A1 | 5/2010 | Conlon | | EP | 1875876 A1 | 1/2008 |
| 2010/0152539 A1 | 6/2010 | Ghabrial et al. | | EP | 1891881 A1 | 2/2008 |
| 2010/0152609 A1 | 6/2010 | Zwolinski et al. | | EP | 1902663 A1 | 3/2008 |
| 2010/0152746 A1 | 6/2010 | Ceniccola et al. | | EP | 1477106 B1 | 6/2008 |
| 2010/0179510 A1 | 7/2010 | Fox et al. | | EP | 1949844 A1 | 7/2008 |
| 2010/0179530 A1 | 7/2010 | Long et al. | | EP | 1518499 B1 | 8/2008 |
| 2010/0191050 A1 | 7/2010 | Zwolinski | | EP | 1709918 B1 | 10/2008 |
| 2010/0191267 A1 | 7/2010 | Fox | | EP | 1985226 A2 | 10/2008 |
| 2010/0198149 A1 | 8/2010 | Fox | | EP | 1994904 A1 | 11/2008 |
| 2010/0198244 A1 | 8/2010 | Spivey et al. | | EP | 1707130 B1 | 12/2008 |
| 2010/0198248 A1 | 8/2010 | Vakharia | | EP | 0723462 B1 | 3/2009 |
| 2010/0249700 A1 | 9/2010 | Spivey | | EP | 1769749 B1 | 11/2009 |
| 2010/0286791 A1 | 11/2010 | Goldsmith | | EP | 1493397 B1 | 9/2011 |
| 2010/0298642 A1 | 11/2010 | Trusty et al. | | FR | 2731610 A1 | 9/1996 |
| 2010/0312056 A1 | 12/2010 | Galperin et al. | | GB | 330629 A | 6/1930 |
| 2010/0331622 A2 | 12/2010 | Conlon | | GB | 2335860 A | 10/1999 |
| 2010/0331774 A2 | 12/2010 | Spivey | | GB | 2403909 A | 1/2005 |
| 2011/0093099 A1 | 4/2011 | Fox | | GB | 2421190 A | 6/2006 |
| 2011/0098694 A1 | 4/2011 | Long | | GB | 2443261 A | 4/2008 |
| 2011/0098704 A1 | 4/2011 | Long et al. | | JP | 56-46674 | 4/1981 |
| 2011/0105850 A1 | 5/2011 | Voegele et al. | | JP | 63309252 A | 12/1988 |
| 2011/0112434 A1 | 5/2011 | Ghabrial et al. | | JP | 4038960 A | 2/1992 |
| 2011/0115891 A1 | 5/2011 | Trusty | | JP | 8-29699 A | 1/1996 |
| 2011/0124964 A1 | 5/2011 | Nobis | | JP | 2002-369791 A | 12/2002 |
| 2011/0152609 A1 | 6/2011 | Trusty et al. | | JP | 2003-088494 A | 3/2003 |
| 2011/0152610 A1 | 6/2011 | Trusty et al. | | JP | 2003-235852 A | 8/2003 |
| 2011/0152612 A1 | 6/2011 | Trusty et al. | | JP | 2004-33525 A | 2/2004 |
| 2011/0152858 A1 | 6/2011 | Long et al. | | JP | 2004-065745 A | 3/2004 |
| 2011/0152859 A1 | 6/2011 | Long et al. | | JP | 2005-121947 A | 5/2005 |
| 2011/0152878 A1 | 6/2011 | Trusty et al. | | JP | 2005-261514 A | 9/2005 |
| 2011/0152923 A1 | 6/2011 | Fox | | JP | 2006297005 A | 11/2006 |
| 2011/0160514 A1 | 6/2011 | Long et al. | | NL | 1021295 C2 | 2/2004 |
| 2011/0190659 A1 | 8/2011 | Long et al. | | SU | 194230 | 5/1967 |
| 2011/0190764 A1 | 8/2011 | Long et al. | | SU | 980703 | 12/1982 |
| 2011/0245619 A1 | 10/2011 | Holcomb | | WO | WO 84/01707 A1 | 5/1984 |
| 2011/0306971 A1 | 12/2011 | Long | | WO | WO 92/13494 A1 | 8/1992 |
| | | | | WO | WO 93/10850 A1 | 6/1993 |
| FOREIGN PATENT DOCUMENTS | | | | WO | WO 93/20760 A1 | 10/1993 |
| DE | 3008120 A1 | 9/1980 | | WO | WO 93/20765 A1 | 10/1993 |
| DE | 4323585 A1 | 1/1995 | | WO | WO 95/09666 A1 | 4/1995 |
| DE | 19713797 A1 | 10/1997 | | WO | WO 96/22056 A1 | 7/1996 |
| DE | 19757056 B4 | 8/2008 | | WO | WO 96/27331 A1 | 9/1996 |
| DE | 102006027873 B4 | 10/2009 | | WO | WO 96/39946 A1 | 12/1996 |
| EP | 0086338 A1 | 8/1983 | | WO | WO 97/12557 A1 | 4/1997 |

| | | |
|---|---|---|
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048065 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

U.S. Appl. No. 13/036,895, filed Feb. 28, 2011.
U.S. Appl. No. 13/036,908, filed Feb. 28, 2011.
U.S. Appl. No. 13/218,221, filed Aug. 25, 2011.
U.S. Appl. No. 13/267,251, filed Oct. 6, 2011.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastamosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. (2007), pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

U.S. Appl. No. 11/894,358, filed Aug. 21, 2007.
U.S. Appl. No. 11/968,810, filed Jan. 3, 2008.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.

International Seach Report and Written Opinion for PCT/US2010/022181, Mar. 26, 2010 (18 pages).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and immunogenicity by Electroporation In Vivo," The Journal of Immunology, 164, pp. 4635-4640 (2000).

Weaver et al., "Theory of electroporation: A review," Bioelectrochemistry and Bioenergetic, 41, pp. 135-160 (1996).

Muller et al, "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castelivi et al., "Hybrid Transvaginal NOTES Sleeve Gastrectorny in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakke Retractors, obtained Aug. 25, 2009 (5 pages).
Zadno et al., "Linear Superelasticity in Cold-Worked NI-TI," Engineering Aspect of Shape Memory Alloys, pp. 414-419 (1990).
U.S. Appl. No. 12/696,598, flied Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 26, 2011.
U.S. Appl. No. 13/013,147, filed Jan. 25, 2011.
U.S. Appl. No. 12/000,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.

* cited by examiner

SURGICAL ACCESS DEVICE

BACKGROUND

Endoscopy refers to looking inside a human body for medical reasons using an instrument called an endoscope. Endoscopy is a minimally invasive diagnostic medical procedure used to evaluate interior surfaces of an organ or other tissue by inserting a small tube into the body, often, but not necessarily, through a natural body opening of a patient or through a relatively small incision. Using the endoscope, a surgeon may view surface conditions of the organs or other tissue, including abnormal or diseased tissue such as lesions and other various surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region, referred to generally herein as a surgical site.

Laparoscopic surgery is a minimally invasive surgical technique in which operations are performed through small incisions (usually 0.5 cm-1.5 cm) or keyholes, as compared to the larger incisions required in traditional open-type surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single-chip or three-chip). Also attached is a fiber-optic cable system connected to a "cold" light source (halogen or xenon) to illuminate the operative field and configured to be inserted through a 5 mm or 10 mm cannula to view the surgical site. The abdomen is usually insufflated with carbon dioxide gas to create a working and viewing space for a surgeon. Stated another way, the abdomen is essentially blown up like a balloon (i.e., insufflated) thereby elevating the abdominal wall above the internal organs like a dome. Carbon dioxide gas can be used for the insufflation because it is common to the patient's body and can be removed by the respiratory system if it is absorbed through tissue.

Minimally invasive therapeutic procedures used to treat diseased tissue by introducing medical instruments to the surgical site through a natural opening of a patient are known as Natural Orifice Translumenal Endoscopic Surgery (NOTES™). In general, there are a variety of systems for inserting an endoscope through a natural opening in the human body, dissecting a lumen, and then, treating the inside of the abdominal cavity. For example, in U.S. Pat. No. 5,297,536 to Wilk, issued on Mar. 29, 1994, which is hereby incorporated by reference in its entirety, a sample treatment system is disclosed. This system is comprised of a dissecting device for perforating a lumen wall, an endoscope insert member for inserting an endoscope, a tube, an endoscope, and a pneumoperitoneum device for deflating the abdominal cavity, and a closing device.

When transluminal endoscopic surgery is carried out using the above-referenced system or any other suitable system, an overtube can first be inserted through a natural opening in the patient's body (e.g., mouth, anus, or vagina). A distal end of the overtube may be attached to an organ wall or other tissue by vacuum pressure, thus being temporarily fixed thereon such that the organ wall or other tissue can be punctured. An incising instrument, such as a needle, for example, may be passed through the overtube from a proximal end of the overtube to a distal end of the overtube, and/or through a working channel of the endoscope, and used to puncture and create an opening through the organ wall or other tissue. An inflatable member, such as a medical balloon, for example, may be positioned in the opening and then inflated to enlarge the opening. Once the opening has been enlarged by the inflatable member, the inflatable member can be at least partially deflated and removed from the body and/or retracted into the overtube and the overtube may then be inserted into and partially through the opening to serve as a working channel for the endoscope and/or other surgical instruments or devices to the surgical site. After surgery of the inside of the organ or other tissue is complete, the overtube may be removed from the enlarged opening so that the opening can be closed by an O-ring or other suitable closure device and then the endoscope and the overtube may be withdrawn from the body.

In various techniques, difficulties may arise when inserting the inflatable member through the working channel of the endoscope, through the overtube, through the organ wall, and/or through other tissue. In various circumstances, the inflatable member could be breached if it catches or snags a portion of the working channel, such as an end of the working channel, for example, a portion of the overtube, a portion of the organ wall, and/or other tissue. Additionally, the inflatable member can be prematurely inflated in the overtube owing to subatmospheric pressure conditions within the overtube and surrounding the outside walls of the inflatable member. Accordingly, in the field of endoscopy, there remains a need for improved methods and devices for inserting an inflatable member into position in the opening of the organ wall or other tissue during an endoscopic surgical procedure.

FIGURES

The novel features of the various embodiments are set forth with particularity in the appended claims. The various embodiments, however, both as to organization and methods of operation may best be understood by reference to the following description, taken in conjunction with the accompanying figures as follows.

DESCRIPTION

Figure 1:
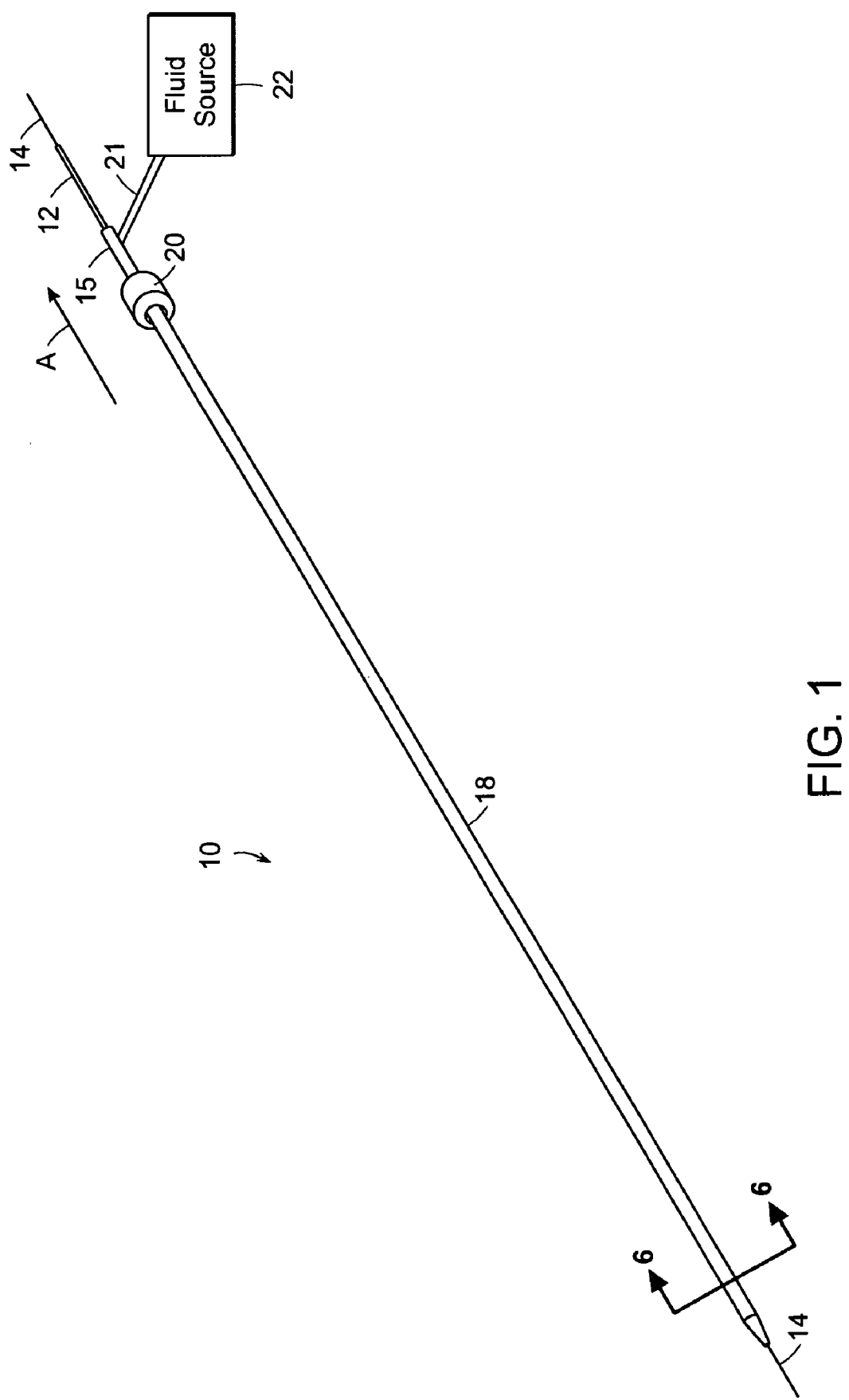
FIG. 1 illustrates a perspective view of a surgical access device comprising an inflatable member covered by a protective sleeve in a first position in accordance with one non-limiting embodiment.

It will be appreciated that the terms "proximal" and "distal" are used herein with reference to a clinician, a surgeon, or a user ("surgeon") manipulating one end of an instrument or device that protrudes out of a patient (i.e., a natural orifice). The term "proximal" refers to a portion of the instrument or device closest to the surgeon and the term "distal" refers to a portion of the instrument located furthest from the surgeon. It will be further appreciated that for conciseness and clarity, spatial terms such as "vertical," "horizontal," "up," and "down" may be used herein with respect to the figures. Surgical instruments or devices, however, may be used in many orientations and positions and, as such, these terms are not intended to be limiting and absolute.

During the course of various surgical procedures, such as in intraluminal and transluminal procedures, for example, there often exists a need to create a surgical space for advancing overtubes and surgical instruments or devices and/or for allowing a surgeon to access a surgical site. Inflatable members, such as medical balloons, for example, may be used to enlarge an opening or incision ("opening") in an organ wall or other tissue created by a needle, a needle knife, or other cutting, piercing, incising, or puncturing member ("needle"). In various embodiments, the needle can be hollow such that the most distal ends of the needle can puncture the tissue. In one embodiment, the most distal ends of the needle can comprise cutting, incising, or piercing members. Various inflatable members are commercially available from Boston Scientific Corporation, C. R. Bard, Inc., and Cook Medical Inc., for example. In at least one embodiment, the needle can be a Veress needle or a Rotary needle, for example. Various needles are commercially available from Ethicon Endo-Surgery, Inc. and Covidien Ltd. In other various embodiments, a guidewire with a cutting, piercing, incising, or puncturing member on a distal end thereof can be used, alone or in combination with a needle or hollow needle, to create the opening (hereafter the term "needle" can encompass such guidewire embodiments).

In various embodiments, a hollow conduit can be introduced into a natural opening in a patient's body. In at least one embodiment, the conduit can be inserted into an overtube which has been inserted into the natural opening in the patient's body. In any event, the needle can be introduced into the natural opening of the patient's body through a proximal end of the conduit and can be fed through a distal end of the conduit to access an organ wall or other tissue ("tissue"), for example. In at least one embodiment, an endoscope can be inserted into the overtube through the proximal end of the overtube and extend through or near the distal end of the overtube. In such an embodiment, the conduit can be positioned within a working channel of the endoscope and can extend from a distal end thereof to allow the conduit and the needle to gain access to the tissue proximate to a surgical site or a surgical access site. In various embodiments, the needle and the conduit can be flexible and/or can comprise flexible portions.

In various embodiments, an uninflated inflatable member, such as a medical balloon, for example, can be attached to, sealed to, positioned on, surround, or can be integrally formed with or on at least a portion of an outer surface of a distal portion of the conduit, for example, and can be introduced into the opening in the tissue created by advancing the needle distally through the tissue. The inflatable member can then be transitioned from an uninflated or a collapsed state to an inflated or an expanded state thereby radially or otherwise displacing side walls of the opening to create a larger opening or surgical space in the tissue such that the enlarged opening can receive a portion of the endoscope, a portion of the overtube, and/or portions of other surgical instruments or devices, for example, therethrough. In at least one embodiment, the inflatable member can be at least partially comprised of a flexible material.

In various embodiments, an inflation conduit can surround a portion of the conduit and can extend at least from a fluid source to a proximal portion of the inflatable member such that the inflatable member can be expanded with fluid from the fluid source owing to a distal portion of the inflatable member being sealed to a portion of the conduit and/or another member positioned on, attached to, and/or formed with or on the conduit. In still other various embodiments, distal portions of the inflatable member can be sandwiched between the member positioned on, attached to, or integrally formed with or on the conduit and a portion of the conduit, for example. In one embodiment, the inflation conduit can comprise an inner diameter or perimeter larger than the outer diameter or perimeter of the conduit to allow the fluid from the fluid source to flow or be pumped into and out of the inflatable member. The fluid from the fluid source can flow or be pumped through a void created between the outer diameter or perimeter of the conduit and the inner diameter or perimeter of the inflation conduit, for example. In other embodiments, the flow of the fluid can at least partially displace the outer surface of the conduit and the inner surface of the inflation conduit to flow to the inflatable member. In any event, a distal portion of the inflation conduit can be attached or sealed to and in fluid communication with the proximal portion of the inflatable member with a distal portion of the inflatable member being attached or sealed to a portion of the conduit or to a member positioned on, attached to, or integrally formed on or with the conduit such that the inflatable member can be inflated by the fluid. In other various embodiments, the inflation conduit can be eliminated and end portions of the inflatable member can be sealed to the conduit. In such an embodiment, the conduit can be in fluid communication with the fluid source at its proximal portion and can be in fluid communication with the inflatable member at its distal portion through an opening, aperture, slot, or perforation (not illustrated) in the conduit. As a result, the fluid from the fluid source can be flowed or pumped into the conduit and through the opening, aperture, slot, or perforation, which can be in fluid communication with an internal area of the inflatable member to inflate the inflatable member.

One problem encountered by various devices is that the uninflated inflatable member is not protected while it is being fed through the overtube, the working channel of the endoscope, and/or while it is being advanced through the opening in the tissue. As the inflatable member is made of a thin and flexible material, such as polyethylene terephthalate glycol, polyurethane, plastic, nylon, or combinations thereof, for example, it can be somewhat susceptible to tearing or puncturing. In one embodiment, the inflatable member can included longitudinally oriented pleats positioned about a perimeter of the inflatable member when the inflatable member is in a deflated configuration. In some instances, the inflatable member can tear, puncture, or become unpleated when it is contacted with a sharp end of the working channel, for example.

Further, the inflatable member can sometimes at least partially inflate prior to being positioned within the opening in the tissue owing to subatmospheric pressure conditions within the overtube. These subatmospheric pressure conditions can cause the inflatable member to prematurely inflate if the inflatable member is in fluid communication with atmospheric pressure or with a space having a higher pressure than the subatmospheric pressure conditions within the overtube. Even if a valve is supplied between the inflatable member and an atmospheric pressure space, any fluid within the conduit and/or the inflation conduit may cause the inflatable member to at least partially inflate owing to the fluid remaining within the conduit and/or the inflation conduit intermediate the valve and the inflatable member. Such premature inflation can cause delays during a surgical procedure as a partially inflated inflatable member may not fit properly into the opening in the tissue. To at least partially alleviate or eliminate the above-referenced difficulties, a surgical access device is provided with a protective sleeve which can, in some circumstances, at least partially cover the inflatable member at appropriate times during a surgical procedure to prevent, inhibit, or at least minimize opportunities for tearing, puncturing, unpleating, and/or premature inflation of the inflatable member.

Figure 2:
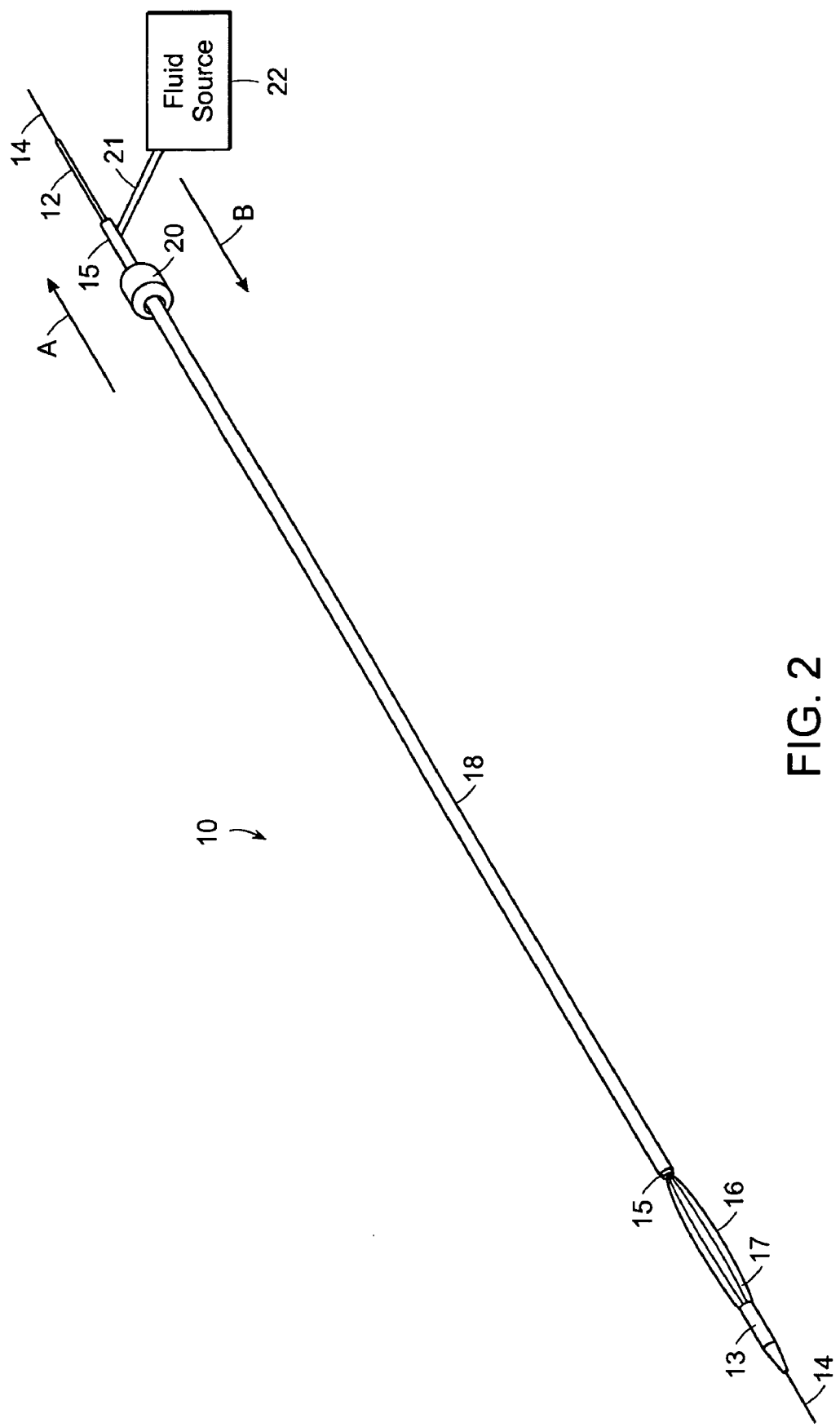
FIG. 2 illustrates a perspective view of the surgical access device of FIG. 1 with the protective sleeve in a retracted or second position to expose the inflatable member in accordance with one non-limiting embodiment.
Figure 3:
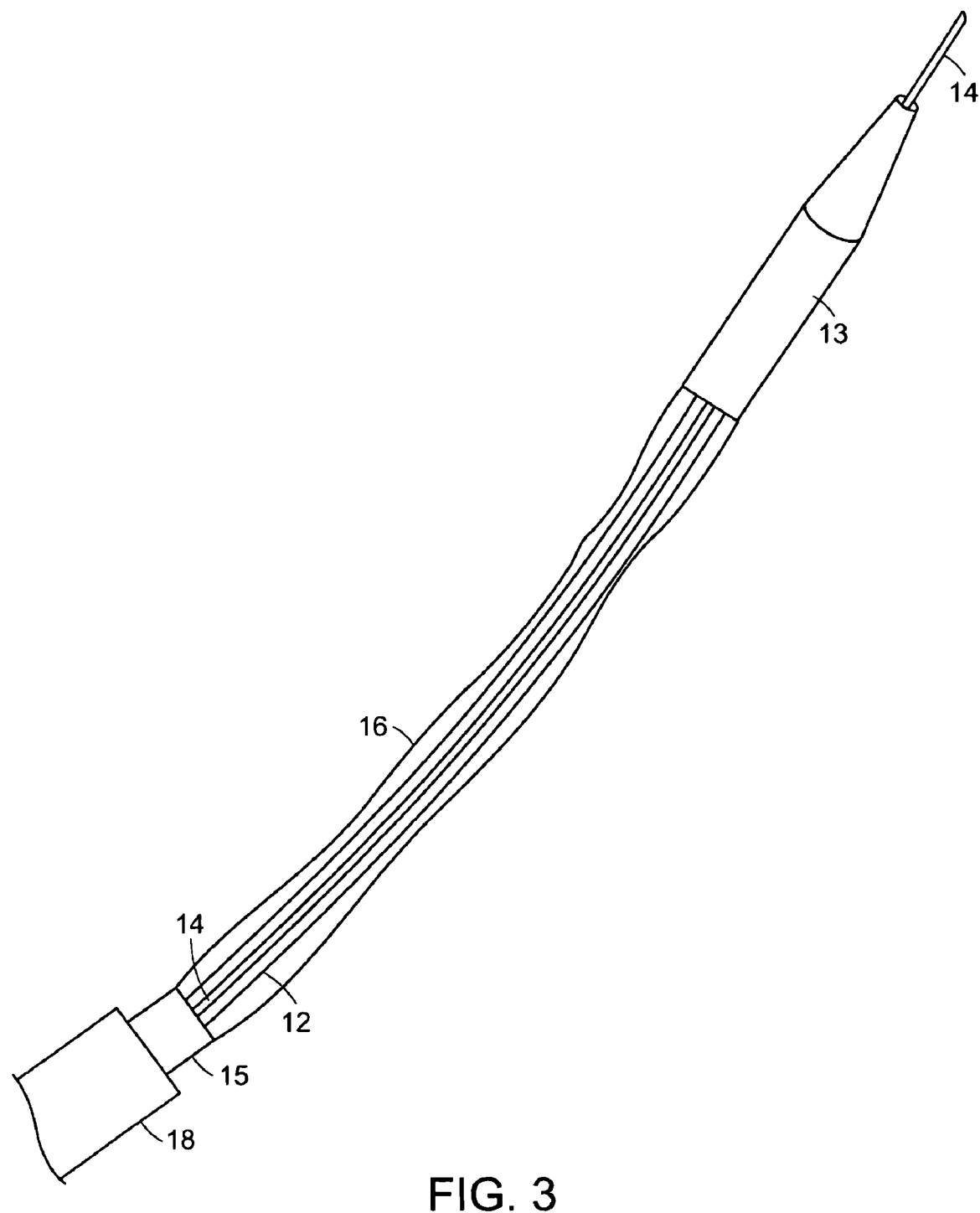
FIG. 3 illustrates an exploded view of the exposed inflatable member of FIG. 2 in accordance with one non-limiting embodiment.
Figure 4:
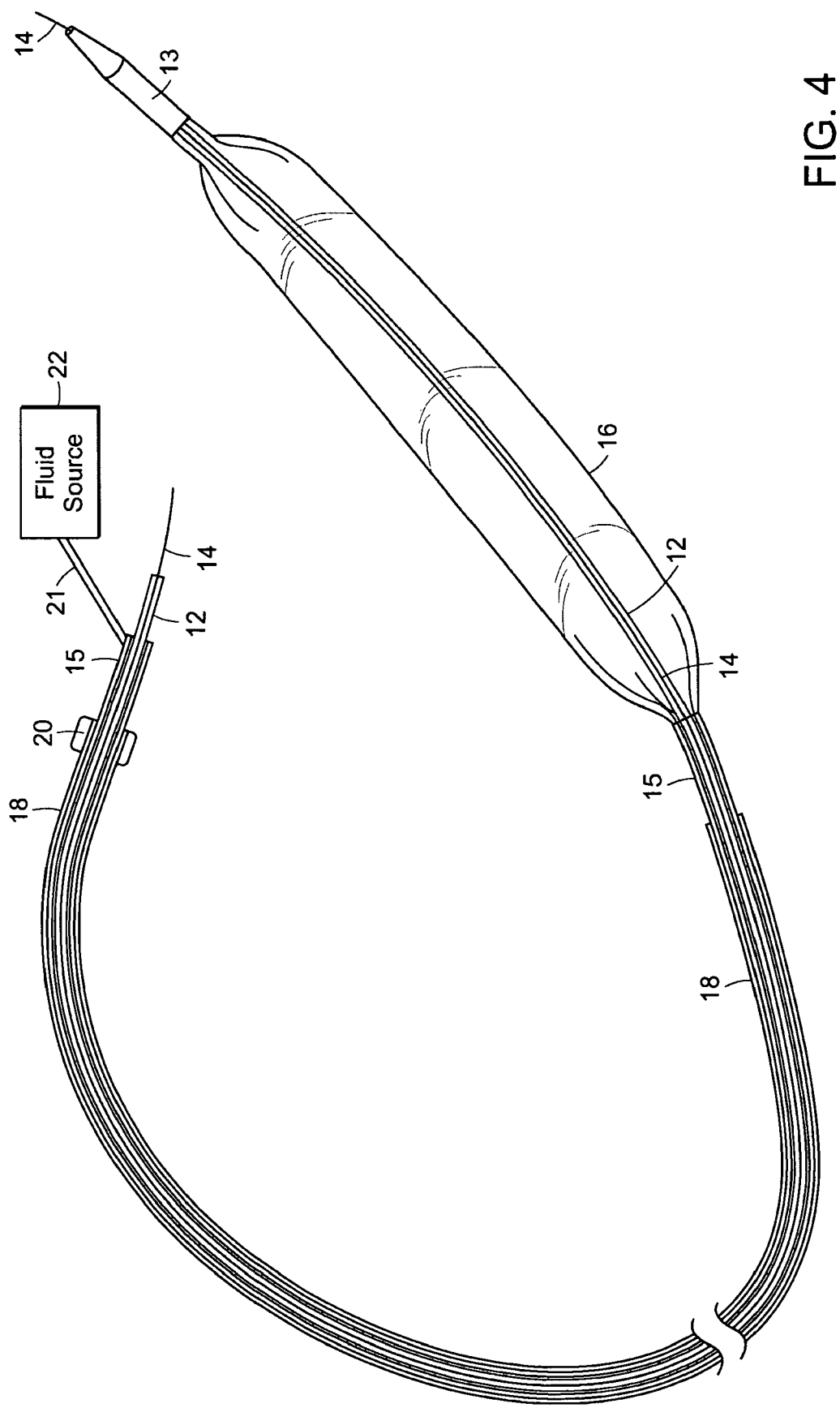
FIG. 4 illustrates a perspective view of a surgical access device where a protective sleeve is in a retracted or second position and an inflatable member is exposed and inflated through the use of a fluid source in accordance with one non-limiting embodiment.
Figure 5:
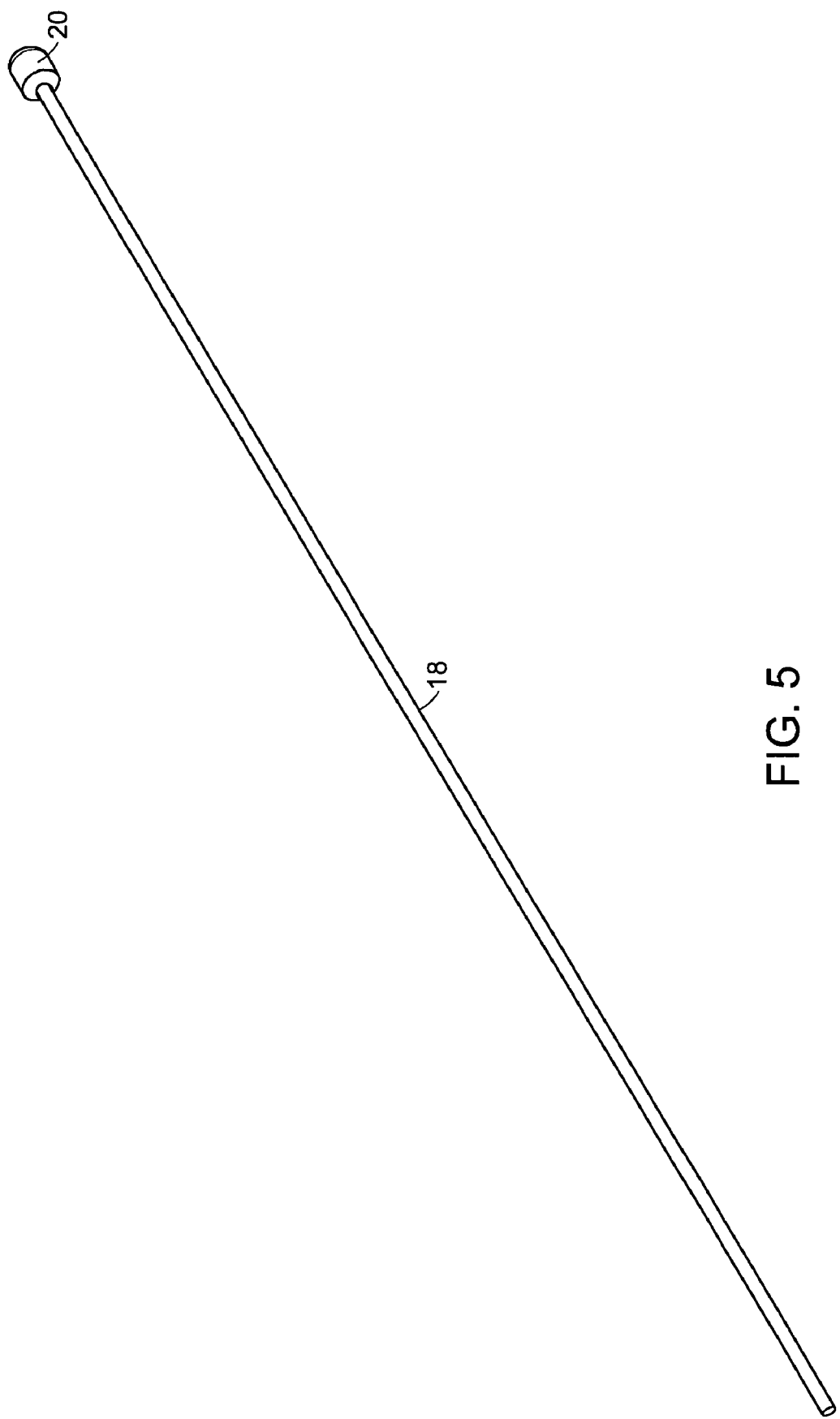
FIG. 5 illustrates a perspective view of the protective sleeve of the surgical access device of FIG. 1 in accordance with one non-limiting embodiment.

In various embodiments, referring to FIGS. 1 and 2, a surgical access device 10 is illustrated. The surgical access device 10 can comprise a conduit 12, a needle 14 configured to be positioned within and at least partially through the distal end of the conduit 12, an optional inflation conduit 15 surrounding at least a portion of the conduit 12, an inflatable member 16 attached to, sealed to, positioned on, surrounding, or integrally formed with or on an outer surface of a distal portion of the conduit 12, and a protective sleeve 18 optionally comprising a handle or handle device 20 on its proximal portion. The protective sleeve 18 is configured to be positioned at least partially over (i.e., at least partially cover) the inflatable member 16 at appropriate times during a surgical procedure to protect and shield the inflatable member 16 from tearing, puncturing, unpleating, and/or premature inflation, for example. In at least one embodiment, the surgical access device 10 can be inserted into and extend through a distal end of a working channel of an endoscope positioned within an overtube, as described in further detail below. In various embodiments, the surgical access device 10, via its various components, can be used to puncture tissue to create an opening therein and then expand the opening using the inflatable member 16, such that an overtube, the endoscope, and/or another surgical instrument or device can be advanced distally through the opening to gain access to a surgical site.

In various embodiments, referring to FIGS. 1-4, the conduit 12 can comprise a hollow elongate opening therethrough and can be long enough to extend from outside of a natural opening in the patient's body to a surgical access site and/or the surgical site. The conduit 12 may be formed of or may comprise a flexible material to allow at least its distal portion to travel through the tortuous path within the patient's body to and at least partially through the opening in the tissue. The needle 14 can be sized and configured to fit and be slidable within the hollow elongate opening in the conduit 12. In use, the needle 14 can be inserted into the proximal end of the conduit 12 and fed through the conduit 12 until it extends from the distal end of the conduit 12. As referenced above, the needle 14 can be used to create, puncture, pierce, incise, and/or cut the opening in the tissue.

Further to the above, still referring to FIGS. 1-4, at least portions of the inflatable member 16 can be integrally formed with, integrally formed on, positioned on, sealed to, or attached to the outer surface of the distal portion of the conduit 12. In various embodiments, the inflatable member 16 can fully or partially surround the distal portion of the conduit 12 while the inflation conduit 15 can surround at least portions of the conduit 12 between the fluid supply 22 or tube 21 and the proximal portion of the inflatable member 16. As the inflatable member 16 can surround the distal portion of the conduit 12, it may have a larger, or slightly larger, perimeter or diameter than the perimeter or diameter of the conduit 12 it its uninflated state. Likewise, as the inflation conduit 15 can surround a portion of the conduit 12, it can have a larger, or slightly larger, perimeter or diameter than the perimeter or diameter of the conduit 12. In one embodiment, the inflatable member 16 can also comprise a plurality of longitudinally oriented pleats 17. These pleats 17 can be positioned about the perimeter or diameter of the inflatable member 16, as illustrated in FIG. 2. In some instances, it can be important to maintain the pleats 17 when the inflatable member 16 is in the uninflated position to enable to the inflatable member 16 to be properly inflated. It will be appreciated that more than one inflatable member can be used with the surgical access device 10 as is recognized by those of ordinary skill in the art. Further, the inflatable member can comprise any suitable inflatable member or inflatable members known to those of ordinary skill in the art.

In at least one embodiment, the inflatable member 16 can be in fluid communication with a fluid source 22 configured to provide a fluid to fill or inflate the inflatable member 16 at an appropriate time during the surgical procedure. In various embodiments, the fluid source 22 can be in fluid communication with the inflatable member 16 through the conduit 12 and an aperture in the conduit which is in fluid communication with the inflatable member 16. In other embodiments, the fluid source 22 can be in fluid communication with the inflatable member 16 through the inflation conduit 15 and an optional tube 21 connecting the fluid source 22 and the inflation conduit 15. As discussed above, the inflation conduit 15 can extend at least from the proximal portion of the inflatable member 16 to the tube 21 (or the inflatable member 15 can extend directly to the fluid source 22) and can have an inner diameter or perimeter larger than the outer diameter or perimeter of the conduit 12. As such, a void can be formed intermediate the inner surface of the inflation conduit 15 and the outer surface of the conduit 12. The inflatable member 16 can also be attached or sealed with the conduit 12 or other member 13 on the conduit 12 at its distal portion and can be in fluid communication with the inflation conduit 15 at its proximal portion such that the inflatable member 16 can be inflated by the fluid source 22. The fluid from the fluid source 22 can then be flowed or pumped through the tube 21, through the void, and then into the inflatable member 16 to inflate the inflatable member 16. In one embodiment, the inflation conduit 15 can be attached to a portion of the conduit 12 such that as the conduit 12 is advanced distally, in the direction indicated by arrow "B" of FIG. 2, the inflation conduit 15 is also advanced distally, in the direction indicated by arrow "B" of FIG. 2.

In various embodiments, the inflation of the inflatable member 16 can be controlled via a control unit (not illustrated) external to the patient that can be operated by the surgeon. In other embodiments, the inflatable member 16 can be inflated by the surgeon activating a manual pump or other suitable inflation device (not illustrated), for example. In various embodiments, the inflatable member 16 can be filled with a fluid in liquid or gas form, such as saline, air, water, and/or carbon dioxide, for example, as such fluids are common to the patient's body and can be easily absorbed and/or exhausted by the body. In various embodiments, as the inflatable member 16 is filled with the fluid, the inflatable member 16 can expand radially outward from the conduit 12 to enlarge the size of the opening in the tissue. It will be appreciated that the inflatable member 16 could also expand in any other suitable fashion depending on the configuration of the inflatable member 16 and the particular surgical need.

In various embodiments, referring to FIGS. 1-6, the protective sleeve 18 can be movable between a first position (see e.g., FIG. 1), where it can cover, or at least partially cover, the uninflated inflatable member 16, and a second position (see e.g., FIG. 2), where it can at least partially expose the inflatable member 16 for inflation. In at least one embodiment, a surgeon can slide the protective sleeve 18 between the first position and the second position (or into any other suitable intermediate position) by applying a proximal-to-distal force to the protective sleeve 18, in the direction indicated by arrow "B" of FIG. 2 (i.e., pushing), or by applying a distal-to-proximal force, in the direction indicated by arrow "A" of FIGS. 1 and 2 (i.e., pulling), to the protective sleeve 18. An optional handle device 20 may be integrally formed with or on or attached to a proximal portion of the protective sleeve 18 to facilitate slidable movement of the protective sleeve 18 relative to the conduit 12. It will be appreciated by those of ordinary skill in the art that any suitable handle or gripping device can be used with the surgical access device 10. Further, the handle device 20 can be eliminated and the surgeon can instead directly grasp the proximal portion of the protective sleeve 18 to move the protective sleeve 18 between the first and the second positions and any other suitable positions.

Figure 6:
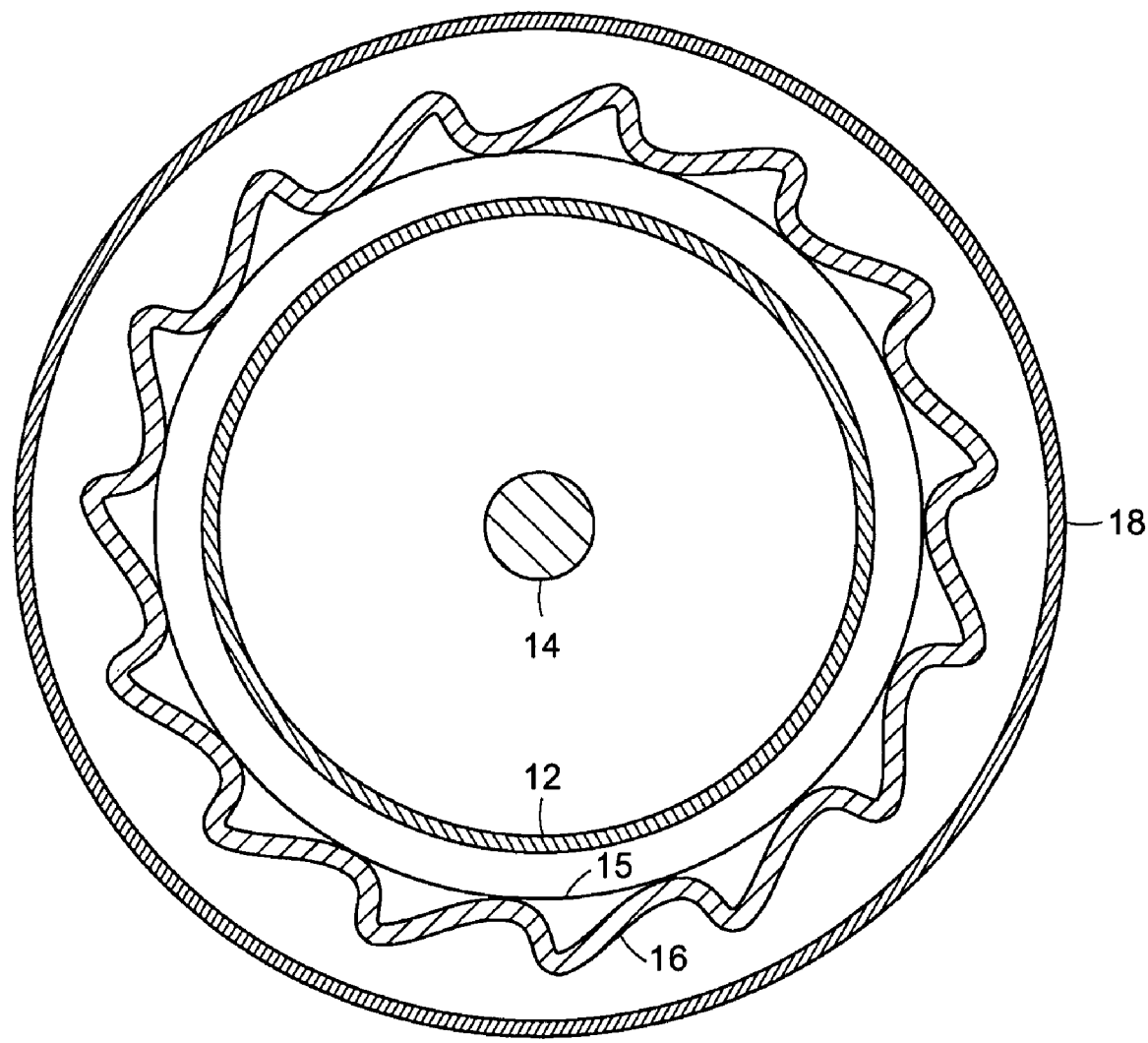
FIG. 6 illustrates a cross-sectional view of the surgical access device taken along line 6-6 of FIG. 1 in accordance with one non-limiting embodiment.

In one embodiment, the protective sleeve 18 may be slidably coupled to the conduit 12 and/or to the inflation conduit 15 in any suitable manner. For example, the protective sleeve 18 may be frictionally engaged with the conduit 12 and/or the inflation conduit 15 or may be otherwise slidably coupled to the conduit 12 and/or the inflation conduit 15. In one embodiment, the protective sleeve 18 and/or the handle 20 of the protective sleeve 18 and the conduit 12 and/or the inflation conduit 15 may be threadably connected, for example. The protective sleeve 18 and/or the handle 20 can have female threads formed on an inner surface thereof and the conduit 12 or the inflation conduit 15 can have male threads formed on an outer surface thereof such that the threads on the protective sleeve 18 and/or the handle 20 can engage the threads on the outer surface of the conduit 12 or the inflation conduit 15 and thereby advance, in the direction indicated by arrow "B" of FIG. 2, or retract, in the direction indicated by arrow "A" of FIGS. 1 and 2, when either the protective sleeve 18, the handle 20, the conduit 12, and/or the inflation conduit 15 is rotated by the surgeon. It will be appreciated by those of ordinary skill in the art that any other suitable mechanical members can be used to advanced and/or retract the protective sleeve 18 with respect to the conduit 12 and/or the inflation conduit 15. In other various embodiments, the advancement and retraction of the protective sleeve 18 can be automated through the use of at least one actuator, for example. For additional clarity, FIG. 6 illustrates a cross-sectional view taken along line 6-6 of FIG. 1 to illustrate how the protective sleeve 18, the inflatable member 16, the inflation conduit 15, the conduit 12, and the needle 14 can be situated when the protective sleeve 18 is in the first position. As referenced above, in various embodiments, the needle 14 can be hollow, for example.

In various embodiments, the protective sleeve 18 can have an inner diameter or perimeter which is larger than a respective outer diameter or perimeter of the conduit 12, the inflation conduit 15, and the uninflated inflatable member 16 to enable the protective sleeve 18 to at least partially or fully surround and slide over a portion of the conduit 12, a portion of the inflation conduit 15, and/or at least a portion the uninflated inflatable member 16. In at least one embodiment, apertures, cut-outs, slots, and/or joints may be formed on the protective sleeve 18 to make the device lighter and/or for various surgical reasons, such as, for example, to add flexibility to the protective sleeve 18 and/or to facilitate the steerability of the protective sleeve 18. Also, the protective sleeve 18 can be formed of or comprise a transparent or semi-transparent material (see e.g., FIG. 4). In at least one embodiment, the protective sleeve 18 may be formed of or may comprise a lubricious, low coefficient of friction material, such as polyethylene, polyetheretherketone (PEEK®), polytetrafluoroethylene (TEFLON®), plastic, nylon, ethylene, and/or a combination thereof, for example, to enable easy sliding movement of the protective sleeve 18 over the conduit 12, the inflation conduit 15, and/or the uninflated inflatable member 16. In such an embodiment, the lubricious, low coefficient material can also help prevent, inhibit, or at least minimize any opportunities for the protective sleeve 18 from tearing or puncturing the uninflated inflatable member 16 when sliding over the uninflated inflatable member 16 and/or when sliding from between the first position and the second position and/or into any suitable intermediate position. In various embodiments, the protective sleeve 18 further can at least inhibit unpleating of the pleats 17 of the inflatable member 16 when the protective sleeve 18 is in the first position thereby leading to more uniform inflation of the inflatable member 16. In various embodiments, the protective sleeve 18 can be flexible as required for traveling along the tortuous path inside the patient's body to the surgical site or surgical access site. In other various embodiments, portions of the protective sleeve 18 can be flexible while other portions can be rigid or semi-rigid, for example. As previously discussed, the protective sleeve 18 may comprise additional features to enhance its flexibility and/or steerability.

FIGS. 7-11 illustrate the surgical access device 10 at various stages of deployment through a cross-section of tissue 32. In use, the surgical access device 10 can be configured to be slidably received within an overtube 24 and an endoscope 26 comprising at least one working channel 28. The endoscope 26 can be any suitable endoscope known to those of ordinary skill in the art. In various embodiments, the overtube 24 can first be inserted into a natural orifice of a patient's body. In at least one embodiment, the endoscope 26 can then be positioned within and extend at least partially through the overtube 24 or extend to or from a distal end 30 of the overtube 24. In at least one embodiment, the distal end 30 of the overtube 24 can engage the tissue 32 and can apply suction to the tissue 32 owing to the subatmospheric pressure conditions created within the overtube 24. The overtube 24 can be in fluid communication with any suitable suction source such as a vacuum pump, for example, (not illustrated) or other suitable vacuum producing device. At least one appropriate end seal (not illustrated) may be provided to maintain the subatmospheric pressure conditions within the overtube 24. These subatmospheric pressure conditions within the overtube 24 can cause a portion of the tissue 32 proximate to a surgical access site to be pulled or drawn into the overtube 24 to locate the tissue 32 for puncturing by the needle 14 portion of the surgical access device 10. The suction applied to the tissue 32 at the distal end 30 of the overtube 24 can at least partially offset any proximal-to-distal (i.e., pushing) force, in the direction indicated by arrow "B" of FIG. 2, being applied to the tissue 32 when the needle 14 or surgical access device 10 is advanced through the tissue 32.

As referenced above, if the proximal end of the conduit 12 and/or inflation conduit 15 is open to atmospheric pressure (i.e., not sealed), or even if the conduit 12 and/or the inflation conduit 15 comprises a valve and/or a seal at a proximal portion thereof, the inflatable member 16 could still, at least partially, prematurely inflate owing to the subatmospheric pressure conditions within the overtube 24. As previously discussed, premature inflation of the inflatable member 16 can cause the inflatable member 16 to be enlarged such that it may not fit within the opening in the tissue 32 created by the needle 14. To address this issue, the protective sleeve 18 may be located in the first position to prevent, inhibit, or at least minimize such premature inflation from occurring by containing the inflatable member 16 within the elongate opening of protective sleeve 18 and thus inhibiting, for example, the inflatable member 16 from expanding outwardly relative to the conduit 12 prior to an appropriate time during a surgical procedure. Stated another way, the protective sleeve 18 can surround the inflatable member 16 closely enough to at least inhibit the inflatable member 16 from prematurely inflating. Furthermore, to any extent that the inflatable member 16 may partially inflate due to the tolerances of manufacturing, the inflatable member 16 can be contained within the hollow elongate opening defined by the protective sleeve 18 and, thus, can be inhibited from inflation by the protective sleeve 18, for example.

Figure 7:
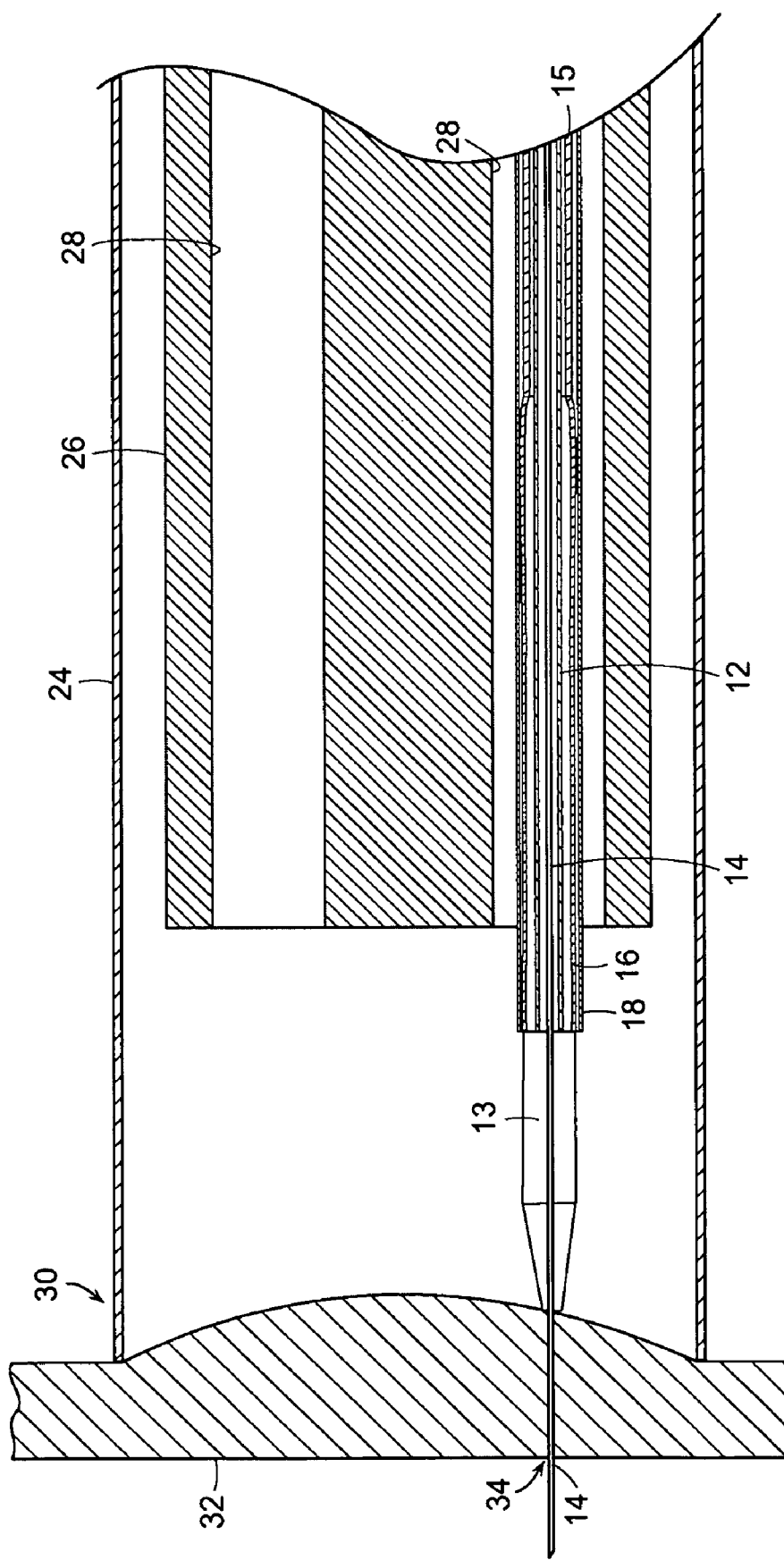
FIG. 7 illustrates a cross-sectional view of a distal portion of the surgical access device of FIG. 1 extending through a working channel of an endoscope and creating an opening in tissue to allow access to a surgical site in accordance with one non-limiting embodiment.
Figure 8:
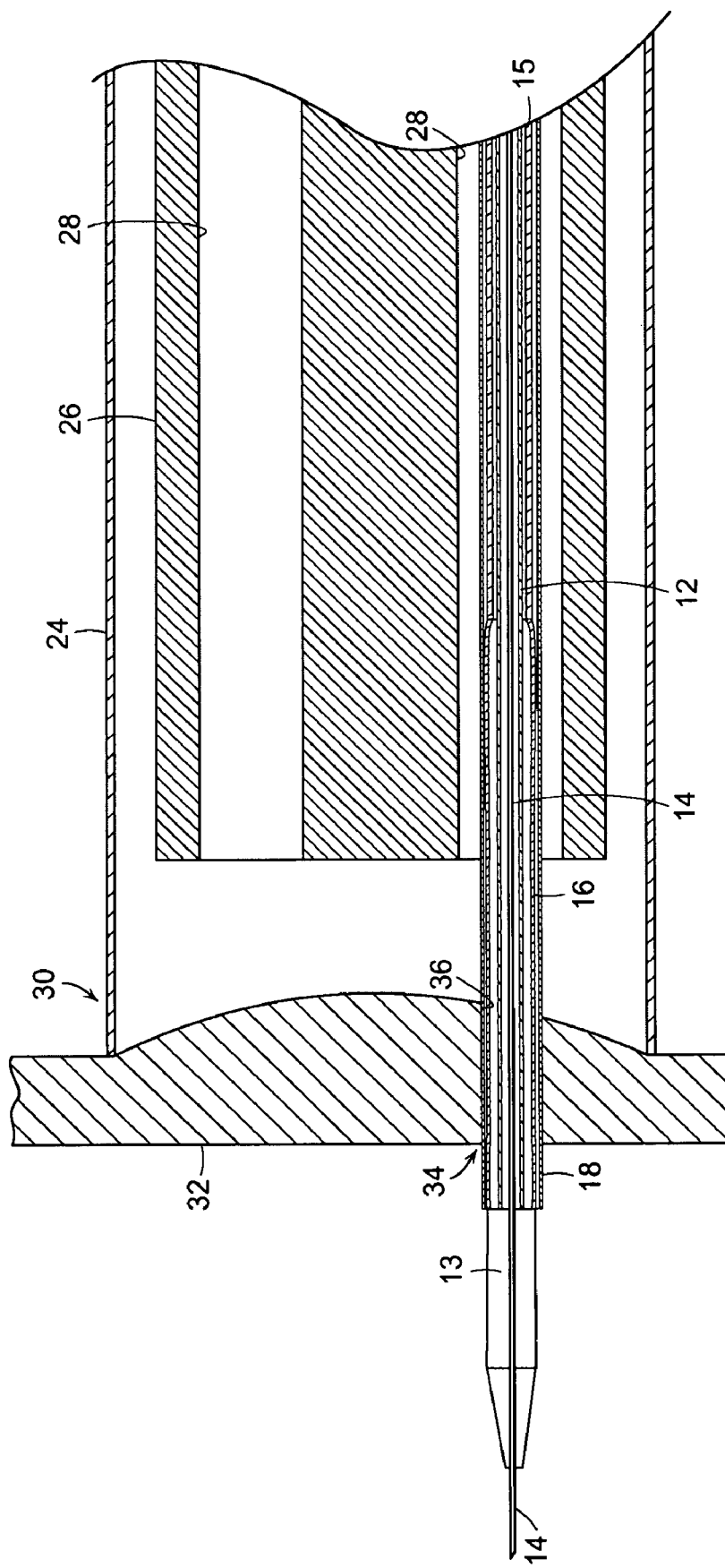
FIG. 8 illustrates a cross-sectional view of the distal portion of the surgical access device of FIG. 7 with the protective sleeve in a first position and being advanced through the opening in the tissue in accordance with one non-limiting embodiment.

Further to the above, referring to FIGS. 7 and 8, while the suction is applied to the tissue 32 by the overtube 24, the needle 14 can be advanced distally towards the tissue 32 to puncture or pierce the tissue 32 and create an initial "needle sized" opening 34 therein. The surgeon can accomplish this advancement by applying a proximal-to-distal (i.e., pushing) force, in the direction illustrated by arrow "B" of FIG. 2, to a proximal portion of the needle 14. Once the needle 14 has punctured or pierced the tissue 32 and has created the opening 34, the conduit 12 and thereby the inflatable member 16, owing to the inflatable member's position on or attachment to, for example, the distal portion of the conduit 12 and the relative stretchability of the tissue 32, can be advanced distally toward, into, and at least partially through the opening 34 in the tissue 32. This advancement can be accomplished by the surgeon applying a proximal-to-distal (i.e., pushing) force to the proximal portion of the conduit 12, in the direction indicated by arrow "B" of FIG. 2. During the advancement of the conduit 12 and the inflatable member 16, the protective sleeve 18 can also be advanced by the surgeon again applying a proximal-to-distal (i.e., pushing) force to the proximal portion of the protective sleeve 18 and/or to the handle device 20, in the direction indicated by arrow "B" of FIG. 2, to maintain the inflatable member 16 in a shielded or protected state (i.e., the first position). FIG. 8 illustrates one stage of deployment of the surgical access device 10 through the cross-section of tissue 32. As illustrated, the protective sleeve 18, along with the conduit 12 and the inflatable member 16, can be advanced at least partially through the opening 34 in the tissue 32 with the protective sleeve 18 in the first position to cover the uninflated inflatable member 16. In this manner, the protective sleeve 18 shields the uninflated inflatable member 16 and protects it from puncturing, tearing, and/or unpleating during the advancement stage of deployment. The protective sleeve 18 generally should be advanced through the opening 34 in the tissue 32 while in the first position, although the conduit 12 and the inflatable member 16 could be advanced through the opening 34 when the protective sleeve 18 is in the second position or in any other suitable intermediate position.

Figure 9:
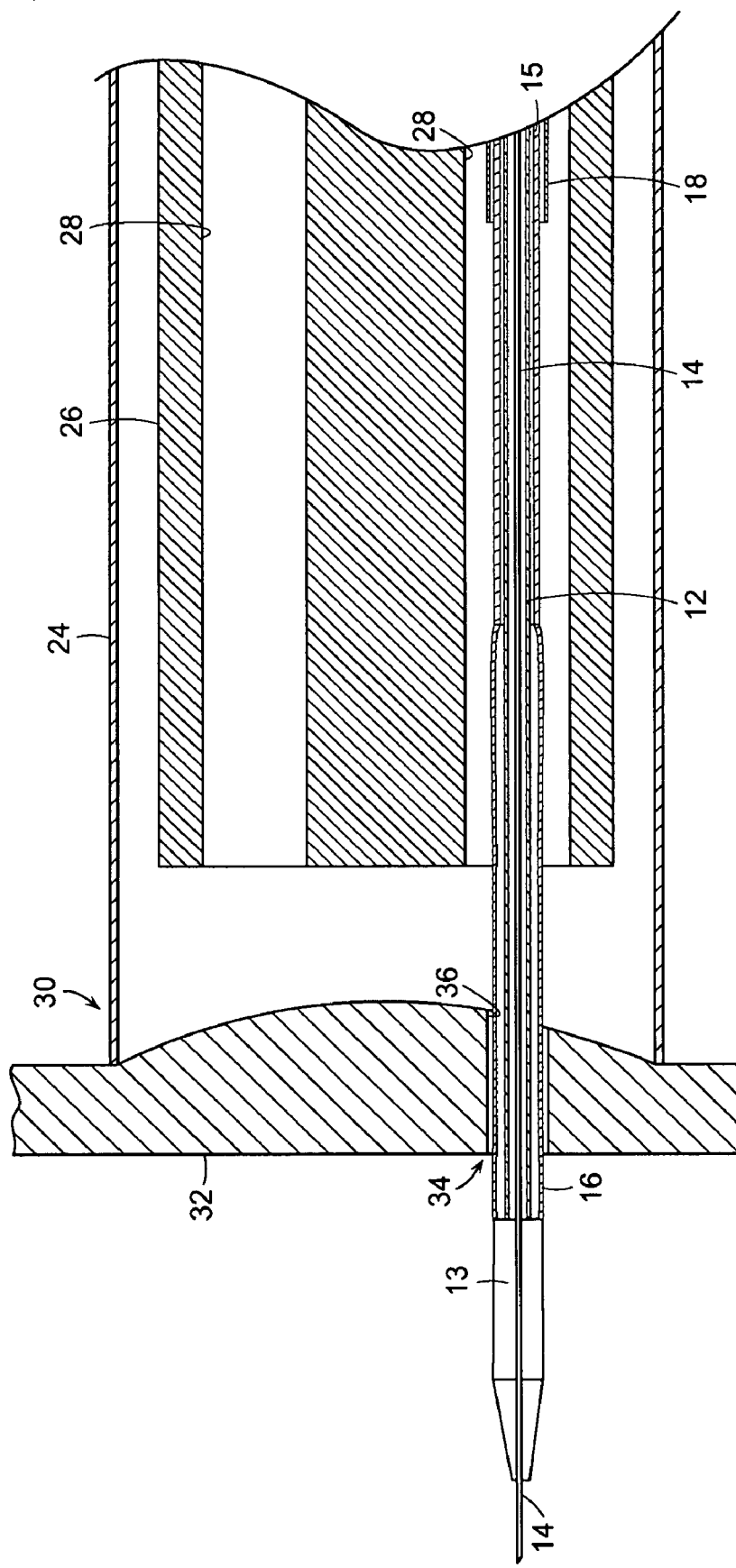
FIG. 9 illustrates a cross-sectional view of the distal portion of the surgical access device of FIG. 8 after the protective sleeve has been retracted into the second position to expose the inflatable member to the opening in the tissue in accordance with one non-limiting embodiment.

In various embodiments, referring to FIG. 9, once the protective sleeve 18, the conduit 12, and the uninflated inflatable member 16 are advanced through the opening 34 in the tissue 32, the protective sleeve 18 can be retracted into the second position. This retraction can be accomplished by the surgeon applying a distal-to-proximal (i.e., pulling or retracting) force, in the direction indicated by arrow "A" of FIGS. 1 and 2, to the proximal portion of the protective sleeve 18 and/or to the optional handle device 20. As illustrated in FIG. 9, when the protective sleeve 18 is retracted into the second position, the inflatable member 16 can be exposed such that it can be inflated via the conduit 12 or inflation conduit 15 and the fluid source 22 to expand the opening 34 in the tissue 32.

Figure 10:
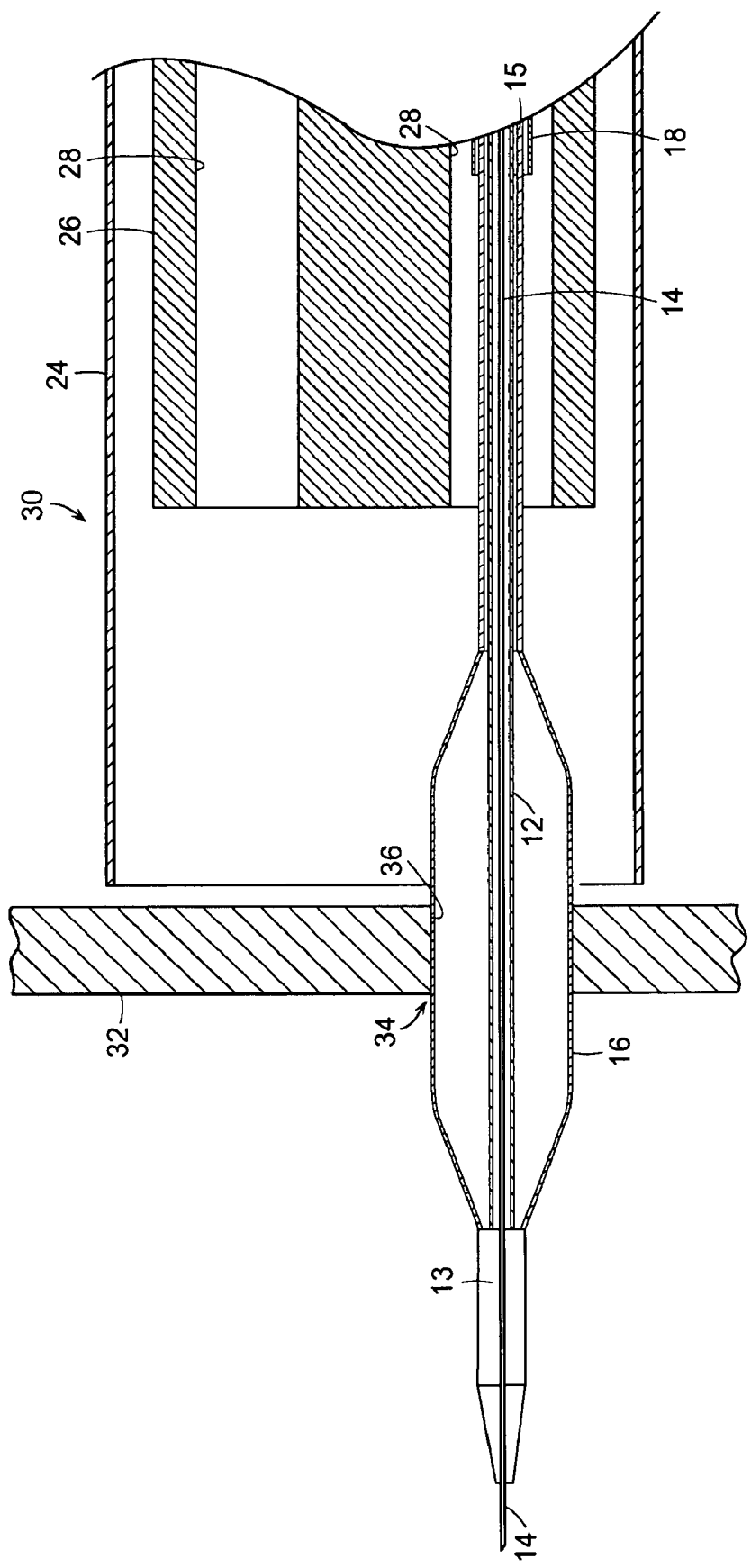
FIG. 10 illustrates a cross-sectional view of the distal portion of the surgical access device of FIG. 9 after the protective sleeve has been retracted into the second position and with the inflatable member partially inflated to expand the opening in the tissue in accordance with one non-limiting embodiment.
Figure 11:
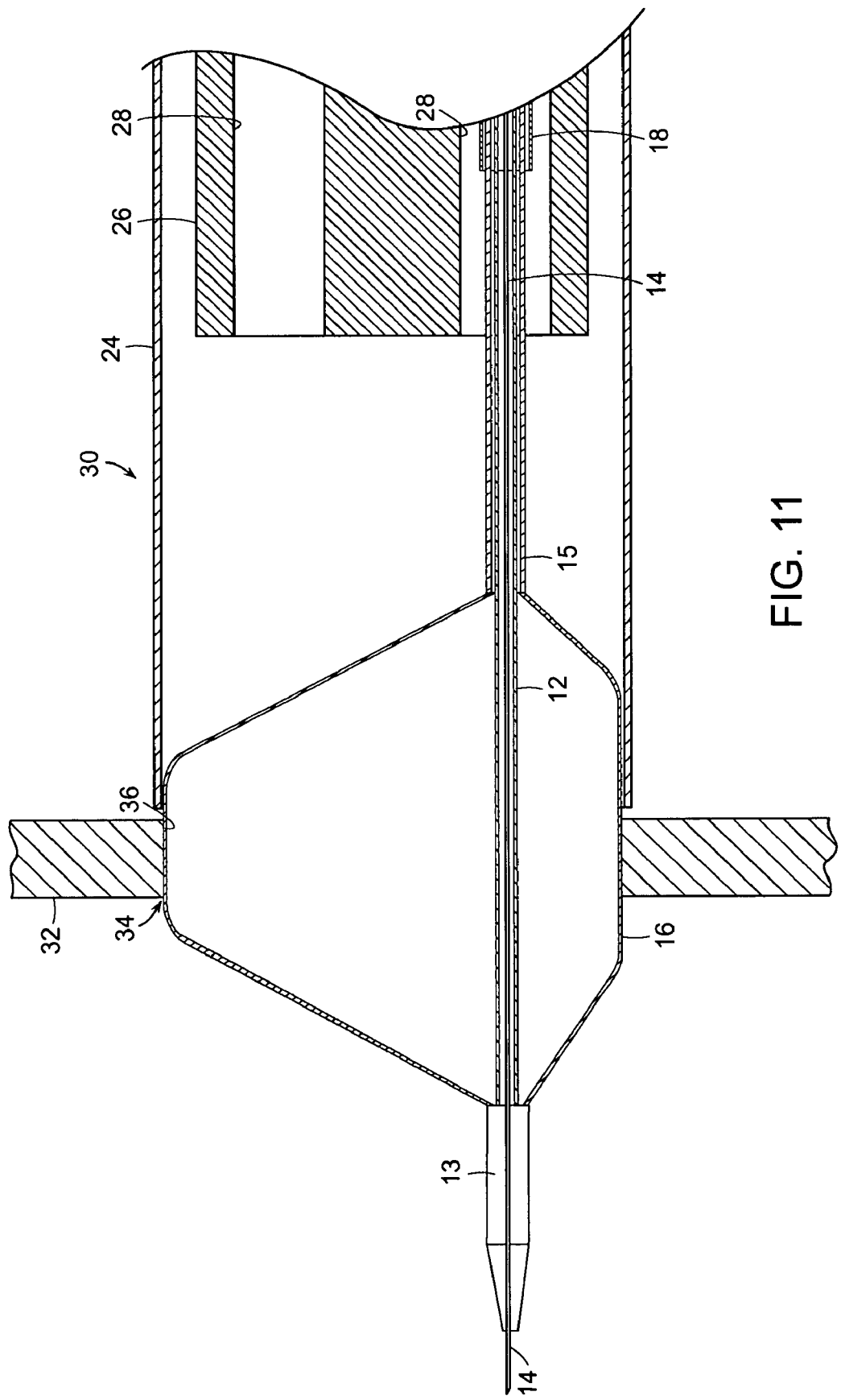
FIG. 11 illustrates a cross-sectional view of the distal portion of the surgical access device of FIG. 9 after the protective sleeve has been retracted into the second position and with the inflatable member sufficiently inflated to expand the opening in the tissue in accordance with one non-limiting embodiment.

In various embodiments, referring to FIGS. 10 and 11, before the inflatable member 16 is inflated, however, the distal end 30 of the overtube 24 can optionally be withdrawn from contact with the tissue 32 to alleviate, eliminate, or at least minimize the suction being applied to the tissue 32. Alternatively, the vacuum source could be powered off, for example, while maintaining the distal end 30 of the overtube 24 in contact with or proximate to the tissue 32. The fluid supply 22 (see e.g., FIGS. 1, 2, and 4) can then flow a fluid into the inflatable member 16 through the inflation conduit 15 to inflate the inflatable member 16. Alternatively, the fluid could be flowed through the conduit 12, as discussed above. As the inflatable member 16 is filled with the fluid, the inflatable member 16 can apply a force to the sidewalls 36 of the opening 34 created in the tissue 32 to radially or otherwise expand the opening 34 given the relatively elastic properties of the tissue 32. This expansion can continue until the opening 34 is large enough to accommodate the distal portion of the overtube 24, the distal portion of the endoscope 26, and/or a distal portion of other surgical instruments therethrough, for example.

In various embodiments, referring to FIG. 11, the inflatable member 16 can be inflated to a size that is similar to, the same as, slightly smaller than, and/or slightly larger than a diameter or a perimeter of the overtube 24. In various embodiments, a proximal portion of the inflatable member 16 can be at least partially inflated within the distal end 30 of the overtube 24 such that the overtube 24 can easily be advanced distally through the tissue 32 without tearing the tissue or to at least minimize tearing of the tissue 32, owing to the similarity of the diameter or perimeter of the overtube 24 and the diameter or perimeter of the inflatable member 16, for example. In other various embodiments, the inflatable member 16 can be inflated to a size that is similar to, the same as, slightly smaller than, and/or slightly larger than a diameter or a perimeter of the endoscope 26, for example, such that the endoscope 26 can be advanced through the tissue 32 in a similar manner as the overtube 30 described above.

Once the opening 34 is expanded to a suitable size by the inflatable member 16 and/or the overtube 24 and/or the endoscope 26 are advanced partially through the opening 34, the fluid can be withdrawn, pumped, or otherwise removed from the inflatable member 16 and flowed back into the fluid supply 22 through inflation conduit 15 or the conduit 12. After a sufficient amount of the fluid, or substantially all of the fluid, is withdrawn from the inflatable member 16, the surgical access device 10 can be withdrawn from the working channel 28 of the endoscope 26. Withdrawal of the surgical access device 10 from the working channel 28 allows other surgical instruments or devices to be inserted into the working channel 28 and extended from the distal end of the working channel 28 to obtain access to the surgical site through the opening 34 in the tissue 32. It will be appreciated that endoscopes may comprise more than one working channel. Accordingly, other surgical instruments may be inserted through any of these additional working channels enabling the surgical access device 10 to remain in-situ, for example, during a surgical procedure.

In various embodiments, the overtube 24 can generally be flexible so as to allow navigation through the tortuous pathway of a body lumen during an endoscopic procedure. The size of the overtube 24 can vary but, in various embodiments, it can have a length that allows it to be inserted translumenally through a patient's esophagus and an inner diameter or perimeter suitable to receive the endoscope 26 therein. The overtube 24 can be made flexible using various techniques. For example, the overtube 24 can be formed from a flexible material and/or it can include one or more features formed therein to facilitate flexibility, such as a plurality of cut-outs or slots, for example. In other embodiments, the overtube 24 can be formed from a plurality of linkages that are movably coupled to one another. The overtube 24 can also include regions that vary in flexibility. For example, certain portions of the overtube 24, such as the distal portion, can be more rigid than other portions of the overtube 24, such as the proximal portion, to correspond to the shape of a body lumen through which the overtube 10 is being inserted. This can be achieved by forming the overtube 24 from different materials, varying the diameter or thickness of the overtube 24, and/or using various other suitable techniques known to those of ordinary skill in the art. A person skilled in the art will appreciate that the overtube 24 can have virtually any configuration that allows the overtube 24 to flex as it is inserted through a tortuous body lumen. The overtube 24 can also include other features to facilitate use, such as one or more spiral wires embedded therein in a configuration to prevent kinking of the overtube 24 during flexure, for example. In various embodiments, the protective sleeve 18, the conduit 12, and/or the inflation conduit 15 can include any suitable features discussed above with respect to the overtube 24, for example.

Figure 12:
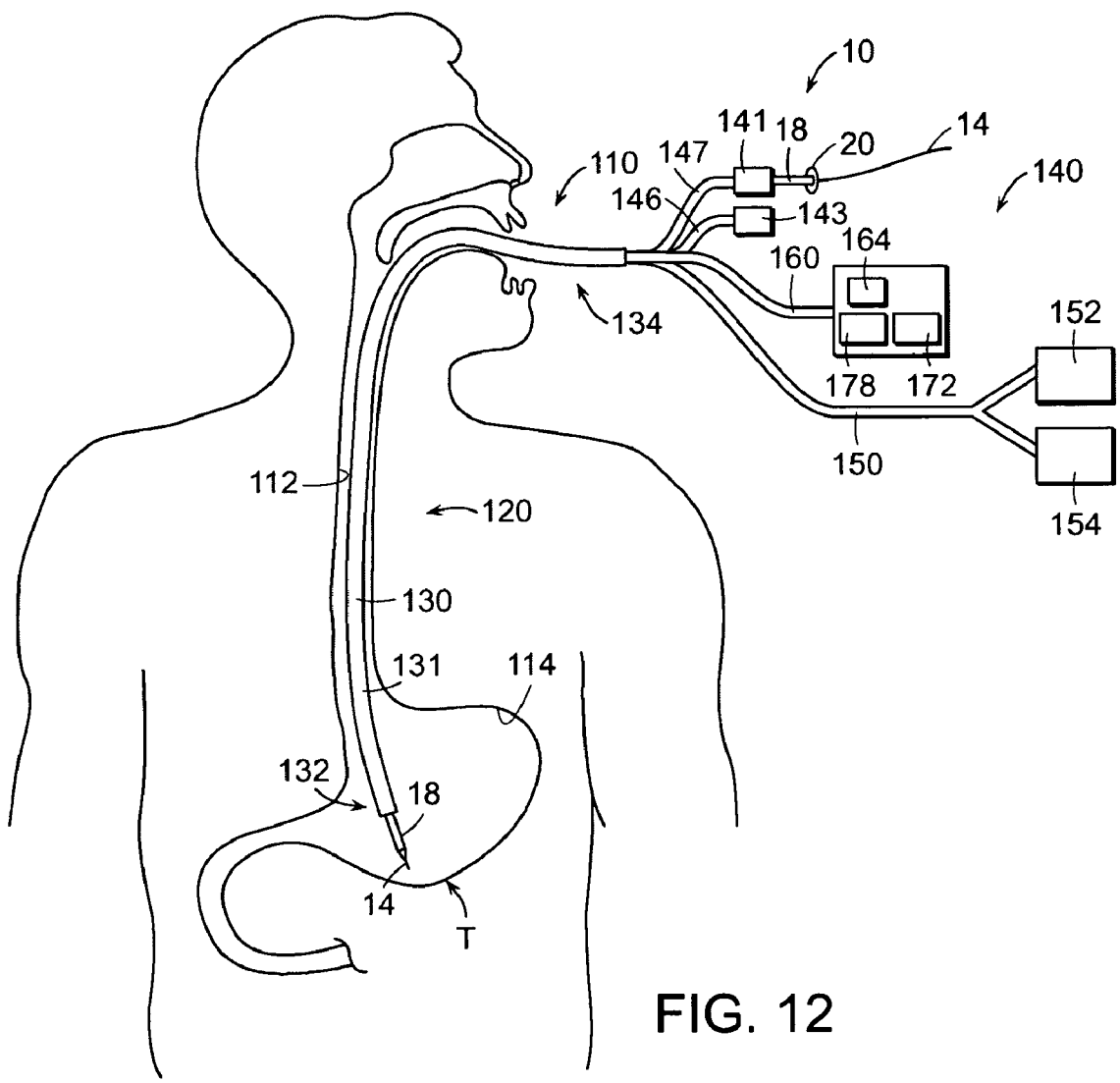
FIG. 12 illustrates a surgical access device being used in conjunction with an overtube, an endoscope having various components and inserted into an upper gastrointestinal tract of a patient in accordance with one non-limiting embodiment.
Figure 13:
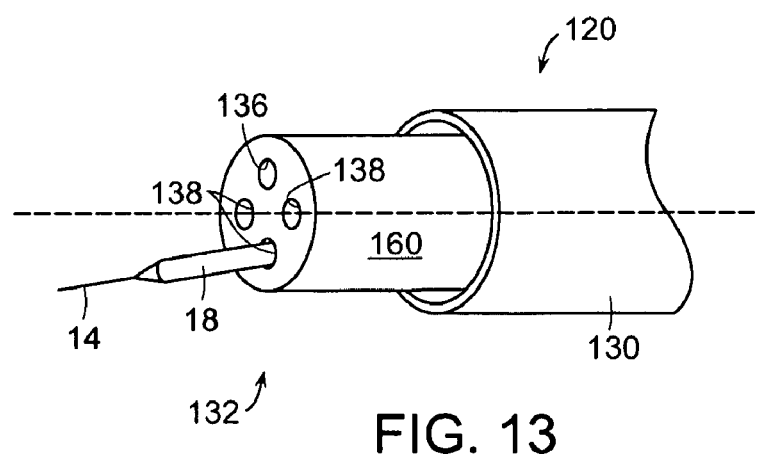
FIG. 13 illustrates a perspective view of a distal portion of a surgical access device extending from a working channel of a distal end of the endoscope of FIG. 12 in accordance with one non-limiting embodiment.

The surgical access device 10 as described herein can have many uses. A non-limiting example of one particular use is described below with reference to FIGS. 12 and 13. In various embodiments, a flexible endoscopic portion 131 of an endoscope 160 (e.g., gastroscope) is inserted into an upper gastrointestinal tract of a patient. FIG. 12 illustrates the surgical access device 10 inserted through a natural orifice such as the mouth 110 and esophagus 112 into the stomach 114 to establish an opening in the stomach 114 for performing a surgical operation such as a gall bladder removal or a cholecystectomy, for example. FIG. 13 illustrates a distal portion 132 of the endoscope 160. As shown in FIGS. 12 and 13, the endoscope 160 may comprise the distal portion 132 and a proximal portion 140. In at least one embodiment, an overtube 130, configured to receive at least the endoscopic portion 131 of the endoscope 160, can be inserted into the mouth 110 and can extend towards and/or into the stomach 114. The overtube 130 can create a working channel for insertion of the endoscopic portion 131 of the endoscope 160. In various embodiments, the overtube 130 may be fabricated from nylon or high-density polyethylene plastic, for example. In various embodiments, the endoscopic portion 131 can define various working channels 138 that extend at least from the natural orifice 110 to the surgical site. In addition, the endoscopic portion 131 may define a viewing port 136, for example. As such, the endoscope 160 may be used for viewing the surgical site within the patient's body. Various cameras and/or lighting apparatuses may be inserted into the viewing port 136 of the endoscope 160 to provide the surgeon with a view of the surgical site.

In the embodiment illustrated in FIG. 12, one of the tools, devices, or surgical instruments that can be accommodated in the working channels 138 is a hollow vacuum/air tube 150 that may be in fluid communication with a fluid source such as at least one of a vacuum source 152 and a pressurized air source 154. In one embodiment, the vacuum/air tube 150 can be sized to receive therein another surgical instrument in the form of the endoscope 160. A variety of different types of endoscopes are known and, therefore, their specific construction and operation will not be discussed in great detail herein. In various embodiments, the endoscope 160 may operably support a video camera that communicates with a video display unit 164 that can be viewed by the surgeon during the surgical procedure. In addition, the endoscope 160 may further comprise a fluid-supply lumen therethrough that is coupled to a source of water 172, saline solution, and/or any other suitable fluid and/or an air supply lumen that is coupled to a source of air 178.

In use, the surgical access device 10 can be inserted into one of the working channels 138 through either working channel port 141 or 143 and then through either working channel tube 146 or 147 to working channel 138 and used to puncture, pierce, create, or incise an opening in tissue "T" proximate to the surgical site. As illustrated in FIGS. 12 and 13, a portion of the surgical access device 10 can extend from the distal end of the working channel 138 to enable access to the tissue "T." In various embodiments, the surgical access device 10 can function as explained herein.

In various embodiments, again referring generally to the various stages of deployment illustrated in FIGS. 7-11, a method of using the surgical access device 10 is provided. First, the surgeon can insert an overtube 24 into a natural opening of a patient, such as the mouth, for example. The surgeon can then either insert a portion of the endoscope 26 into the overtube 24 or can simply insert the surgical access device 10 into the overtube 24. In many instances, the surgeon may insert the portion of the endoscope 26 before inserting the surgical access device 10 to allow the surgeon to view the surgical site via a viewing port of the endoscope 26. In such an instance, the surgeon can position the surgical access device 10 within and at least partially through the working channel 28 of the endoscope 26. As the surgical access device 10 is inserted into the working channel 28 or the overtube 24, the protective sleeve 18 can be in the first position where it at least partially covers, shields, and protects the uninflated inflatable member 16 to prevent, inhibit, or at least minimize tearing, puncturing, and/or unpleating of the uninflated inflatable member 16 during insertion. Once a distal end of the surgical access device 10 reaches the surgical site, the surgeon can then turn on a vacuum producing device to create negative pressure conditions or subatmospheric pressure conditions within the overtube 24. These conditions within the overtube 24 can cause a portion of the tissue 32 near the surgical access site or surgical site to be at least partially drawn into the distal end of the overtube 24 such that the portion of the tissue 32 can be punctured by the needle 14 of the surgical access device 10.

To puncture the portion of the tissue 32, the surgeon can advance the distal end of the needle 14 into and insert it through the portion of the tissue 32 by applying a proximal-to-distal (i.e., pushing) force, in the direction indicated by arrow "B" of FIG. 2, to the proximal portion of the needle 14. After the needle 14 has created the opening 34 in the tissue 32, the surgeon can then advance the distal end of the conduit 12 into and through the opening 34 by applying a proximal-to-distal (i.e., pushing) force, in the direction indicated by arrow "B" of FIG. 2, to the proximal portion of the conduit 12. In such an embodiment, the surgeon can also apply a proximal-to-distal (i.e., pushing) force to the handle device 20 or proximal portion of the protective sleeve 18 to ensure that the protective sleeve 18 remains in the first position during insertion of the distal end of the conduit 12 into and at least partially through the opening 34 in the tissue 32. In other various embodiments, a portion of the protective sleeve 18 can be releasably engaged with a portion of the conduit 12 or a portion of the inflation conduit 15 to prevent, inhibit, or at least minimize sliding of the protective sleeve 18 at inappropriate times during the surgical procedure. As discussed previously, by maintaining the protective sleeve 18 in the first position during insertion into the opening 34 in the tissue 32, the uninflated inflatable member 16 can be substantially protected from puncturing, tearing, unpleating, and/or premature inflation under subatmospheric pressure conditions within the overtube 24. Next, the surgeon can move and/or retract the protective sleeve 18 from the first position to a second position thereby exposing the inflatable member 16 to the sidewalls 36 of the opening 34. As discussed above, the protective sleeve 18 can be moved using the handle device 20 or by pushing or pulling the proximal portion of the protective sleeve 18, for example. Also, as discussed above, this movement of the protective sleeve 18 can be accomplished through the use of other mechanical members, such as threads, for example, or through suitable automated members, for example.

Once the protective sleeve 18 has been retracted into the second position, the surgeon can then activate the fluid supply 22 to begin filling the inflatable member 16 via the inflation conduit 15 or the conduit 12, as discussed above. Filling the inflatable member 16 can cause the opening 34 in the tissue 32 to be enlarged as the inflatable member 16 applies a force to the sidewalls 36 of the opening 34 during expansion. Once the opening 34 has been sufficiently expanded and the inflatable member 16 has been deflated, the surgeon can remove the surgical access device 10 from the overtube 24 or working channel 28 and insert appropriate surgical instruments or devices to begin or continue a surgical procedure.

The devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by the cleaning or replacement of particular pieces, and subsequent reassembly. In particular, the devices can be disassembled, and any number of the particular pieces or parts of the devices can be selectively replaced or removed in any combination. Upon the cleaning and/or replacement of particular parts, the devices can be reassembled for subsequent use either at a reconditioning facility or by a surgical team immediately prior to a surgical procedure. Those skilled in the art will appreciate that the reconditioning of the devices can utilize a variety of techniques for disassembly, cleaning/replacement, and reassembly. The use of such techniques, and the resulting reconditioned devices, are all within the scope of the present application.

Preferably, the various embodiments described herein will be processed before surgery. First, a new or used device is obtained and, if necessary, cleaned. The device can then be sterilized. In one sterilization technique, the device is placed in a closed and sealed container, such as a plastic or TYVEK® bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility. It is preferred that the device is sterilized. This can be done by any number of ways known to those skilled in the art, including beta or gamma radiation, ethylene oxide, or steam.

Although the various embodiments have been described herein in connection with certain disclosed embodiments, many modifications and variations to those embodiments may be implemented. Also, where materials are disclosed for certain components, other materials may be used. The foregoing description and following claims are intended to cover all such modifications and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical access device sized to fit in a working channel of an endoscope and configured to be advanced through a tissue opening to a surgical site, comprising:
   a conduit comprising a proximal end and a distal end;
   an inflatable member at least partially surrounding a portion of the conduit and positioned proximate to the distal end of the conduit; and
   a protective sleeve at least partially surrounding a portion of the conduit and configured to translate within the working channel of the endoscope, the protective sleeve configured to be moved at least between a first position and a second position, the protective sleeve configured to at least partially cover the inflatable member when in the first position and configured to expose the inflatable member when in the second position, the protective sleeve configured to be in the first position when the inflatable member is advanced through the tissue opening to the surgical site.

2. The surgical access device of claim 1, the protective sleeve configured to cover the inflatable member when the protective sleeve is in the first position.

3. The surgical access device of claim 1, comprising a handle device one of attached to and integrally formed with the protective sleeve and positioned near a proximal end of the protective sleeve.

4. The surgical access device of claim 1, the protective sleeve comprised of a low-friction material configured to enable sliding over at least a portion of the inflatable member when moving between the first position and the second position.

5. The surgical access device of claim 1, wherein at least a portion of the conduit and at least a portion of the protective sleeve comprise a flexible material.

6. The surgical access device of claim 1, the conduit configured to receive therethrough at least one of a rotary needle, a veress needle, a cutting member, a puncturing member, a piercing member, and a guide wire.

7. The surgical access device of claim 1, the protective sleeve configured to shield the inflatable member and at least inhibit tearing or puncturing of the inflatable member prior to inflation when the protective sleeve is in the first position.

8. The surgical access device of claim 1, the protective sleeve configured to shield the inflatable member and at least inhibit tearing, puncturing or unpleating of the inflatable member during entry into, traveling within, or exiting from the working channel of the endoscope when the protective sleeve is in the first position.

9. The surgical access device of claim 1, the protective sleeve comprising an elongate passage comprising an inner perimeter sized to at least inhibit the inflatable member from inflating under subatmospheric pressure conditions when the protective sleeve is in the first position.

10. The surgical access device of claim 1, the conduit comprising a first outer perimeter, the inflatable member, in an uninflated state, comprising a second outer perimeter, wherein the second outer perimeter is larger than the first outer perimeter, the protective sleeve comprising an elongate channel comprising an inner perimeter, wherein the inner perimeter is larger than the second outer perimeter.

11. The surgical access device of claim 1, the inflatable member comprising at least two longitudinally oriented pleats positioned about the perimeter of the inflatable member, wherein the protective sleeve is configured to at least minimize unpleating of the pleats of the inflatable member when in the first position.

12. A method of using the surgical access device of claim 1, comprising:
inserting the surgical access device of claim 1 into a natural orifice of a patient with the protective sleeve in the first position; and
retracting the protective sleeve into the second position.

13. A surgical access device sized to fit in a working channel of an endoscope and configured to be passed through punctured tissue to gain access to a surgical site, comprising:
a conduit comprising a proximal end and a distal end;
a needle within the conduit, the needle configured to puncture tissue;
an inflatable member at least partially surrounding a portion of the conduit and positioned proximate to the distal end of the conduit; and
a protective sleeve at least partially surrounding a portion of the conduit and configured to translate within the working channel of the endoscope, the protective sleeve moveable at least between a first position, where the protective sleeve at least partially covers the inflatable member, and a second position, where the inflatable member is exposed, the protective sleeve configured to be in the first position when the inflatable member is passed through the punctured tissue to the surgical site, the protective sleeve comprising an elongate channel comprising an inner perimeter sized to at least inhibit the inflatable member from inflating under subatmospheric pressure conditions when the protective sleeve is in the first position.

14. The surgical access device of claim 13, the protective sleeve configured to cover the inflatable member when the protective sleeve is in the first position.

15. The surgical access device of claim 13, comprising a handle device one of attached to and integrally formed with the protective sleeve and positioned near a proximal end of the protective sleeve, the handle device configured to be used to move the protective sleeve between the first position and the second position.

16. The surgical access device of claim 13, the protective sleeve configured to shield the inflatable member and at least inhibit tearing, puncturing, or unpleating of the inflatable member prior to inflation when the protective sleeve is in the first position.

17. The surgical access device of claim 13, the conduit comprising a first outer perimeter, the inflatable member, in an uninflated state, comprising a second outer perimeter, wherein the second outer perimeter is larger than the first outer perimeter, the protective sleeve comprising an elongate channel comprising an inner perimeter, wherein the inner perimeter is larger than the second outer perimeter.

18. A surgical access device sized to fit in a working channel of an endoscope and configured to be advanced through a tissue opening, comprising:
a conduit comprising a proximal portion and a distal portion, wherein the conduit is configured to receive a needle;
an inflatable member at least partially surrounding a portion of the conduit and positioned proximate to the distal portion of the conduit, the inflatable member comprising an outer perimeter in an at least partially uninflated state; and
a sleeve at least partially surrounding a portion of the conduit and configured to translate within the working channel of the endoscope, the sleeve comprising an elongate channel comprising an inner perimeter larger than the outer perimeter, the sleeve moveable at least between a first position and a second position, the sleeve configured to shield the inflatable member and inhibit tearing or puncturing of the inflatable member when the sleeve is in the first position, and the sleeve configured to expose the inflatable member for inflation when the sleeve is in the second position, the protective sleeve configured to be in the first position when the inflatable member is advanced through the tissue opening.

19. The surgical access device of claim 18, the sleeve configured to cover the inflatable member when the sleeve is in the first position to at least inhibit the inflatable member from inflating under subatmospheric pressure conditions.

* * * * *